United States Patent
Vankawala et al.

(10) Patent No.: US 8,133,994 B2
(45) Date of Patent: Mar. 13, 2012

(54) PREPARATION OF APREPITANT

(75) Inventors: Pravinchandra Jayantilal Vankawala, Hyderabad (IN); Ravi Ram Chandrasekhar Elati, Hyderabad (IN); Naveen Kumar Kolla, Hyderabad (IN); Subrahmanyeswara Rao Chlamala, Hyderabad (IN); Srinivas Gangula, Hyderabad (IN)

(73) Assignees: Dr. Reddy's Laboratories Ltd., Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 896 days.

(21) Appl. No.: 12/089,077

(22) PCT Filed: Oct. 6, 2006

(86) PCT No.: PCT/US2006/039813
§ 371 (c)(1),
(2), (4) Date: Apr. 3, 2008

(87) PCT Pub. No.: WO2007/044829
PCT Pub. Date: Apr. 19, 2007

(65) Prior Publication Data
US 2011/0094321 A1   Apr. 28, 2011

Related U.S. Application Data

(60) Provisional application No. 60/766,544, filed on Jan. 26, 2006, provisional application No. 60/745,198, filed on Apr. 20, 2006, provisional application No. 60/745,201, filed on Apr. 20, 2006, provisional application No. 60/820,632, filed on Jul. 28, 2006.

(30) Foreign Application Priority Data

Oct. 6, 2005   (IN) .............................. 1419/CHE/2005
Oct. 12, 2005  (IN) .............................. 1465/CHE/2005
May 4, 2006    (IN) .............................. 808/CHE/2006

(51) Int. Cl.
*C07D 265/32* (2006.01)
(52) U.S. Cl. ........................................................ 544/174
(58) Field of Classification Search ................... 544/174
See application file for complete search history.

(56) References Cited

U.S. PATENT DOCUMENTS

| 5,637,699 A | 6/1997 | Dorn et al. |
| 5,719,147 A | 2/1998 | Dorn et al. |
| 6,177,564 B1 | 1/2001 | Nelson et al. |
| 6,395,898 B1 | 5/2002 | McNamara et al. |
| 2005/0215786 A1 | 9/2005 | Hands et al. |

FOREIGN PATENT DOCUMENTS

| WO | 95/16679 A1 | 6/1995 |
| WO | 01/96315 A1 | 12/2001 |
| WO | 03/089429 A1 | 10/2003 |

OTHER PUBLICATIONS

Zhao, Matthew M. Practical Asymmetric Synthesis of Aprepitant, a Potent Human NK-1 Receptor Antagonist, via a Stereoselective Lewis Acid-Catalyzed Trans Acetalization Reaction. J. Org. Chem. 67, (2002), 6743-6747.*
Cameron J. Cowden et al., Tetrahedron Letters, vol. 41 (2000), pp. 8661-8664.
Joseph F. Payach et al., Organic Process Research and Development, 2004, 8, pp. 256-259.

* cited by examiner

*Primary Examiner* — Rebecca Anderson
*Assistant Examiner* — Samantha Shterengarts
(74) *Attorney, Agent, or Firm* — Thomas C. McKenzie; Robert A. Franks

(57) ABSTRACT

A process for preparing aprepitant.

14 Claims, 5 Drawing Sheets

R= H or C2-C5 alkyl.

PREPARATION OF APREPITANT

The present invention relates to a process for the preparation of aprepitant and its intermediates. The present invention also relates to a potential process related impurity 3-[1-(3,5-bisfluoromethylphenyl) morpholin-2-one of Formula IIc where R is hydrogen (hereinafter referred to as "spiro derivative of aprepitant") or a physiologically acceptable salt thereof, which is a potential impurity formed in the synthesis of aprepitant of Formula I and a process for the preparation thereof. The present invention also relates to a process for the purification of an aprepitant intermediate containing the spiro derivative and other structure related impurities, in a process to get pure aprepitant substantially free from the said impurities.

Aprepitant is chemically known as 5-[[(2R,3S)-2-[(1R)-1-[3,5-bis(trifluoromethyl) phenyl]ethoxy]-3-(4-fluorophenyl)-4-morpholinyl]methyl]-1,2-dihydro-3H-1,2,4-triazol-3-one and has the structure shown as Formula I.

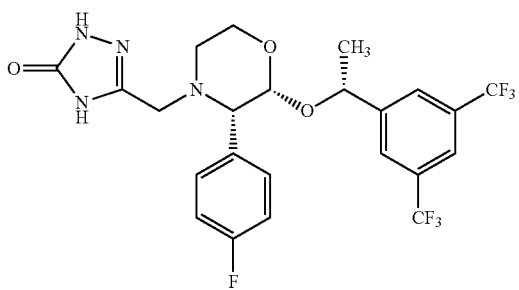

Formula I

Aprepitant is a substance P (neurokinin-1) receptor antagonist useful in the treatment of chemotherapy-induced nausea and vomiting, and is commercially available in the market under the brand name EMEND™ as 80 mg or 125 mg capsules.

More particularly the present invention relates to the identification, preparation and characterization and also the purification method to minimize the said spiro impurity below the limit of detection in the final compound of Formula I and below 1% in the compound of Formula IIb.

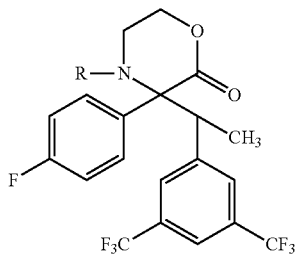

Formula IIc wherein R is hydrogen, $C_2$-$C_5$ alkyl such as ethyl, propyl, isopropyl, butyl, isobutyl, etc.

U.S. Pat. No. 5,719,147 discloses the preparation of aprepitant and its pharmaceutically acceptable salts, a pharmaceutical composition, and methods of treatment. Aprepitant is the cis-isomer of 5-[2-[1-(3,5-Bis-trifluoromethylphenyl)-ethoxy]-3-(4-fluorophenyl)-morpholin-4-ylmethyl]-2,4-dihydro-[1,2,4]triazol-3-one.

International Application Publication No. WO 03/089429 A1 discloses the preparation of aprepitant which involves condensation of the hydrochloride salt of (2R,2-α-R,3S)-2-[1-[3,5-bis(trifluoromethyl)phenyl]ethoxy-3-(4-fluorophenyl)-1,4-oxazine with amidrazone in presence of potassium carbonate and the organic solvents toluene and dimethylsulfoxide to give an intermediate, which on cyclization at 140° C. affords aprepitant. The application also describes the preparation of racemic aprepitant by condensation of the hydrochloride salt of 2-[1-(3,5-bis-trifluoromethylphenyl)ethoxy]morpholine with amidrazone in presence of potassium carbonate and the organic solvents toluene and dimethylsulfoxide to give an intermediate, which is further cyclized at 140° C. to provide the desired compound.

International Application Publication No. WO 01/96315 A1 discloses the preparation of aprepitant by condensation of 3-chloromethyl-1,2,4-triazolin-5-one with 2-(R)-(1-(R)-(3, 5-bistrifluoromethyl) phenyl)ethoxy) 3-(S)-(4-fluorophenyl) morpholine(R)-camphorsulfonic acid salt in the presence of potassium carbonate and N,N-dimethylormamide. Alternatively, aprepitant was prepared by condensation of 3-chloromethyl-1,2,4-triazolin-5-one with 2-(R)-(1-(R)-(3,5-bistrifluoromethyl)phenyl)ethoxy) 3-(S)-(4-fluorophenyl) morpholine paratoluenesulfonic acid salt in the presence of the base N,N-diisopropylethylamine and N,N-dimethylormamide. In another alternative, aprepitant was prepared by condensation of 3-chloromethyl-1,2,4-triazolin-5-one with 2-(R)-(1-(R)-(3,5-bistrifluoromethyl)phenyl)ethoxy)3-(S)-(4-fluoro-phenyl)morpholine paratoluenesulfonic acid salt at 21-23° C. in the presence of the base potassium carbonate and N,N-dimethylormamide.

U.S. Pat. Nos. 5,719,147 and 5,637,699 disclose a process for the preparation of aprepitant which involves condensation of 2(R)-(1-(R)-3,5-bis(trifluoromethyl)phenyl)ethoxy)-3-(S)-(4-fluoro)phenylmorpholine with N-methylcarboxy-2-chloroacetamidrazone in the presence of the base N,N-diisopropylethylamine and the solvent acetonitrile. Subsequent processing by flash chromatography using methylene chloride/methanol/ammonium hydroxide as an eluant in a ratio of 50:1:0.1 provided 2(R)-(1-(R)-3,5-bis(trifluoromethyl) phenyl)ethoxy)-3-(S)-(4-fluoro) phenyl-4-(N-methylcarboxyacetamidrazono)-morpholine, which was further refluxed in xylene and purified by flash chromatography using a 50:1:0.1 ratio of methylene chloride/methanol/ammonium hydroxide as the eluant to afford aprepitant.

The preparation of aprepitant by condensation of 3-chloromethyl-1,2,4-triazolin-5-one with 2-(R)-(1-(R)-(3,5-bistrifluoromethyl) phenyl)ethoxy) 3-(S)-(4-fluorophenyl)-morpholine paratoluenesulfonic acid salt at 0° C. in the presence of potassium carbonate or N,N-diisopropylethylamine and N,N-dimethylformamide with 1% water has also been described by Cameron J. Cowden et al., *Tetrahedron Letters*, Vol. 41 (2000), pp. 8661-8664.

Joseph F. Payach et al., *Organic Process Research and Development*, 2004, 8, pp. 256-259 describes the preparation of aprepitant by reaction of 3,5-bis-trifluoromethylbenzoic acid-4-benzyl-3(S)-(4-fluorophenyl)morpholin-2-ylester with dimethyltitanocene to give 4-benzyl-2-[1-(3,5-bistrifluoromethylphenyl)-vinyloxy]-3-(4-fluorophenyl) morpholine.

U.S. Pat. No. 6,395,898 discloses the preparation of optically pure intermediate compound 2-(R)-(1-(R)-(3,5-bistrifluoromethyl) phenyl)ethoxy) 3-(S)-(4-fluorophenyl) morpholine of Formula IIb of the present invention, which features a highly stereoselective Lewis acid catalyzed transacetylization of (R)-3,5-bistrifluoromethylphenyl ethanol with trichloroacetamidate followed by inversion of the adjacent chiral center on the morpholine ring. The process for the preparation of the chiral alcohol (R)-3,5-bistrifluoromethylphenyl ethanol employs (1S,2R)-cis-1-aminoindan-2-ol and dichloro(p-cymene)Ru(II) dimer as a metal source. This route is industrially and economically not feasible because expensive raw materials such as dichloro(p-cymene)Ru(II) dimer are involved.

Further, the selective substitution reactions are governed by the thermodynamic stability of the intermediates 2-(S)-(3,5-Bis(trifluoromethyl)benzyloxy)-3-(S)-phenylmorpholine is prepared by reaction of 3,5-bis(trifluoromethyl)benzyl alcohol and 2,6-di-t-butyl-4-methylpyridine in the presence of carbon tetrachloride which further treated with trifluoromethanesulfonic anhydride to afford 3,5-Bis (trifluoromethyl) benzyl alcohol, trifluoromethanesulfonate ester.

N-benzyl-3-(S)-phenylmorpholin-2-one was treated with lithium tri(sec-butyl)-borohydride (L-Selectride™) in THF at −75° C., then above obtained 3,5-bis(trifluoromethyl)benzyl alcohol, trifluoromethanesulfonate ester was added, after completion of reaction it was extracted with ethyl acetate and concentrated in vacuo to afford residue. The residue was purified by flash chromatography to afford pure 4-Benzyl-2-(S)-(3,5-bis(trifluoromethyl)benzyloxy)-3-(S)-phenylmorpholine.

The above obtained 4-benzyl-2-(S)-(3,5-bis(trifluoromethyl)benzyloxy)-3-(S)-phenylmorpholine was reduced by Pd/C. The resultant residue was purified by flash chromatography to give pure 2-(S)-(3,5-Bis(trifluoromethyl)benzyloxy)-3-(S)-phenyl-morpholine which are highly sensitive to minor process variations such as temperature, moisture, time, and rate of addition, solvent and thus the processes are practically found to be inconsistent in producing the desired stereochemistry. (R)-(3,5-bis(trifluoromethyl) phenyl)ethan-2-ol is reacted with trichloroimidate in toluene at below −20° C. then quenched via addition of a mixture of 10% brine the trans-glycoside.

U.S. Pat. No. 5,719,147 and International Application Publication No. WO 95/16679 A2 in examples 70 and 75 disclose the preparation of aprepitant of Formula I by a two-step process comprising reacting 2-(R)-(1-(R)-(3,5-bis(trifluoromethyl)-phenyl)ethoxy)-3(S)-(4-fluorophenyl) morpholine with N-methylcarboxy-2-chloroacetamidrazone in the presence of diisopropylethylamine and acetonitrile, to produce an intermediate compound, followed by cyclisation by refluxing in xylene at about 140-150° C. to afford the aprepitant of Formula I.

International Application Publication No. WO 03/089429 A2 discloses the preparation of aprepitant of Formula I comprising the steps of reacting the compound of Formula IIb with a compound of Formula III, in the presence of an inorganic base and toluene to afford the compound of Formula II. The application also discloses the cyclisation of the compound of Formula II at a temperature of 140-150° C. to produce compound of Formula I.

U.S. Pat. No. 6,395,898 discloses the preparation of optically pure key intermediate compound 2-(R)-(1-(R)-(3,5-bistrifluoromethyl) phenyl)ethoxy)-3-(S)-(4-fluorophenyl) morpholine by reduction of 6-[1(S)-3,5-bis(trifluoromethylphenyl)ethoxy]-5-(4-fluorophenyl)-3,6-dihydro-2H-[1,4]oxazine using palladium-carbon as reducing agent.

In summary, some of the disadvantages of the foregoing processes include:
i) the purity of the isolated aprepitant is low, thereby requiring additional steps like flash chromatography, which is industrially not feasible, to obtain a pharmaceutically acceptable substance;
ii) the chemical yield of aprepitant is low;
iii) high temperature reactions are involved;
iv) a lengthy time cycle is required; and
v) expensive reagents are used.

U.S. Pat. No. 6,177,564 B1 discloses the preparation of various intermediates of aprepitant including Formula (XI) which involves treating 4-fluorobenzaldehyde with sodium metabisulfite in methanol/water followed by reaction with sodium cyanide to give 1-cyano-1-(4-fluorophenyl)methanol, followed by treating with N-benzylethanolamine to give the N-benzyl-3-(4-fluorophenyl)-1,4-oxazin-2-one compound of Formula IX of the present invention.

U.S. Pat. No. 5,719,147 discloses the preparation of optically pure intermediate compound N-benzyl-3-(4-fluorophenyl)-1,4-oxazin-2-one of Formula IX of the present invention which involves reaction of (S)-(4-fluorophenyl)glycine with benzaldehyde and sodium borohydride in the presence of sodium hydroxide and methanol to give N-benzyl-(S)-(4-fluorophenyl)glycine, which further is reacted with 1,2-dibromoethane in the presence of N,N-diisopropylamine and N,N-dimethylformamide to give the optically pure compound of Formula IX of the present invention.

Potential impurities in pharmaceutically active agents and formulations containing them include residual amounts of synthetic precursors to the active agent, by-products arising during synthesis of the active agent, residual solvents, isomers of the active agent, excipients used in the preparation of the pharmaceutical formulation, and adventitious substances. Other impurities which may appear on storage include substances resulting from degradation of the active agent, for instance by oxidation or hydrolysis.

It is well known in the art that, for human administration, safety considerations require the establishment, by national and international regulatory authorities, of very low limits for identified, but toxicologically uncharacterized impurities, before an active pharmaceutical ingredient ("API") is commercialized. Typically, these limits are less than about 0.15 percent by weight of each impurity.

Limits for unidentified and/or uncharacterized impurities are obviously lower, typically less than 0.1 percent by weight. Therefore, in the manufacture of APIs, high purity of the active ingredients, such as aprepitant, is required before the manufacture of formulated pharmaceutical products.

It is also known in the art that impurities in an active pharmaceutical 1, ingredient may arise from degradation of the API itself, which is related to the stability of the pure API during storage, and the manufacturing process, including the chemical synthesis. Process impurities include unreacted starting materials, chemical derivatives of impurities contained in starting materials, synthetic by-products, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process.

The product of a reaction is rarely a single compound with sufficient purity to comply with pharmaceutical standards. Side products and by-products of the reaction and adjunct reagents used in the reaction will, in most cases, also be present in the product mixture. At certain stages during processing of an API, such as aprepitant, it must be analyzed for purity, typically, by HPLC or GC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. As discussed above, in the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a high performance liquid chromatography ("HPLC") chromatogram, or a spot on a thin-layer chromatography ("TLC") plate. Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time." The retention time varies daily, or even over the course of a day, based upon the condition of the instrumentation, as well as many other factors. To mitigate the effects such variations have upon accurate identification of an impurity, practitioners use the "relative retention time" ("RRT") to identify impurities. The RRT of an impurity is its retention time divided by the retention time of a reference marker. In theory, aprepitant intermediate itself could be used as the reference marker, but as a practical matter it is present in such a large proportion in the mixture that it can saturate the column, leading to irreproducible retention times, as the maximum of the peak can wander. Thus, it may be advantageous to select a compound other than the API that is added to, or present in, the mixture in an amount sufficiently large to be detectable and sufficiently low as not to saturate the column, and to use that compound as the reference marker.

Those skilled in the art of drug manufacturing research and development understand that a compound in a relatively pure state can be used as a "reference standard." A reference standard is similar to a reference marker, which is used for qualitative analysis only, but is used to quantify the amount of the compound of the reference standard in an unknown mixture, as well. A reference standard is an "external standard," when a solution of a known concentration of the reference standard and an unknown mixture are analyzed using the same technique. The amount of the compound in the mixture can be determined by comparing the magnitude of the detector response.

The reference standard can also be used to quantify the amount of another compound in the mixture if a "response factor," which compensates for differences in the sensitivity of the detector to the two compounds, has been predetermined. For this purpose, the reference standard is added directly to the mixture, and is known as an "internal standard."

The reference standard can even be used as an internal standard when, without the addition of the reference standard, an unknown mixture contains a detectable amount of the reference standard compound using a technique known as "standard addition." In a standard addition, at least two samples are prepared by adding known and differing amounts of the internal standard. The proportion of the detector response due to the reference standard present in the mixture without the addition can be determined by plotting the detector response against the amount of the reference standard added to each of the samples, and extrapolating the plot to zero.

As is known by those skilled in the art, the management of process impurities is greatly enhanced by understanding their chemical structures and synthetic pathways, and by identifying the parameters that influence the amount of impurities in the final product.

It is desirable to provide a simple, industrially feasible, inexpensive, scaleable and safe-to-handle process for the synthesis of the compounds of Formula X and IX which are useful for the preparation of the compound of Formula I.

There remains a need for a simple, industrially feasible, cost effective, scaleable and safe-to-handle process for the synthesis of aprepitant and its intermediates.

SUMMARY OF THE INVENTION

In one aspect, the present invention provides a process for the preparation of aprepitant of Formula I.

An embodiment of a process comprises the steps of:

a) reduction of the racemic compound of Formula IX using a suitable selective reducing agent in the presence of suitable organic solvent(s) to afford a racemic mixture of trans-morpholinol compound of Formula VIII; and b) condensation of the compound of Formula VIII with the compound of Formula VII in the presence of suitable base and organic solvent(s) to afford the racemic mixture of compound of Formula VI;

c) debenzylation of the racemic mixture of the compound of Formula VI using suitable reducing agent in the presence of suitable organic solvent(s) to afford the racemic mixture of the compound of Formula V;

d) diastereomeric crystallization of the compound of Formula V using suitable organic solvent(s) to afford the isomeric mixture compound of Formula IV;

e) resolution of the isomeric mixture compound of Formula IV using suitable chiral reagent in the presence of suitable organic solvent(s) to afford the compound of Formula A4;

f) dehydrogenation of the compound of Formula A4 using suitable dehydrogenating agent the presence of suitable organic solvent(s) to afford the imine compound of Formula IIa;

g) reduction of the imine compound of Formula IIa using suitable reducing agent in presence of suitable organic solvent(s) to afford the amine compound of Formula IIb;

h) condensation of the compound of Formula IIb with the compound of Formula III in the presence of suitable base and organic solvent(s) to afford the compound of Formula II; and i) cyclization of the compound of Formula II in the presence of suitable organic solvent(s) to afford the compound of Formula I.

In another aspect, the present invention relates to a process for the synthesis of the compound N-benzyl-3-(4-fluorophenyl)-1,4-oxazin-2-one of Formula IX, which is an intermediate in the synthesis of aprepitant of Formula I, the process comprising the steps of:

i) hydrolysis of the compound of Formula XI to afford the compound of Formula X using suitable hydrolyzing agent in the presence of suitable base and organic solvent(s); and ii) cyclization of the compound of Formula X using suitable acid or base in the presence of suitable organic solvent(s) to afford the compound of Formula IX.

In another aspect, the present invention provides the intermediate compound of Formula X.

In yet another aspect, the present invention provides processes for purification of aprepitant of Formula I.

In a yet further aspect, the present invention provides a potential spiro impurity of aprepitant of Formula IIc and process for the preparation thereof.

In still another aspect, the present invention there is provided the use of potential spiro impurity of aprepitant of Formula IIc as a reference standard in an analysis of aprepitant of Formula I and Formula IIb.

In another aspect, the invention provides processes for preparing racemic aprepitant.

In a further aspect, the present invention encompasses pharmaceutical compositions comprising aprepitant of Formula I made by the processes of the invention and atleast one pharmaceutically acceptable carrier.

In an embodiment, the invention comprises process for preparing aprepitant, comprising reacting a compound having the formula:

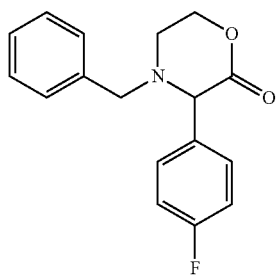

with a selective reducing agent to form an isomeric compound having the formula:

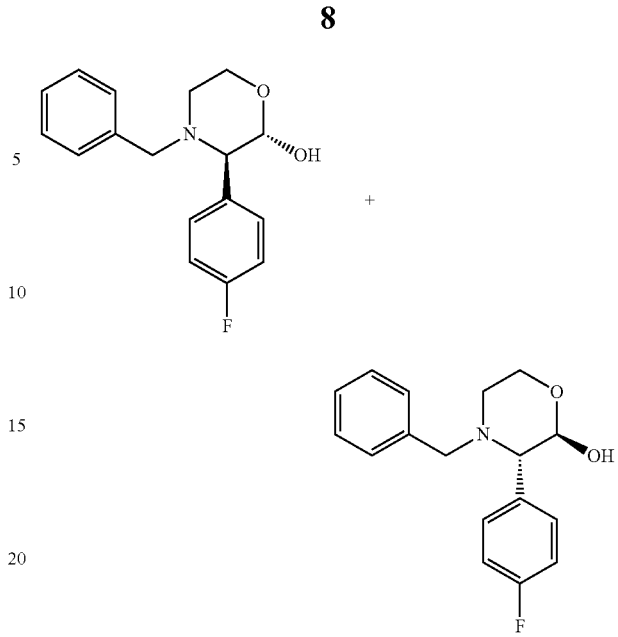

and further reacting with a compound having the formula:

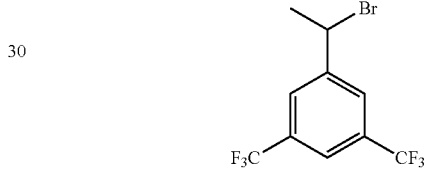

to form an isomeric compound having the formula:

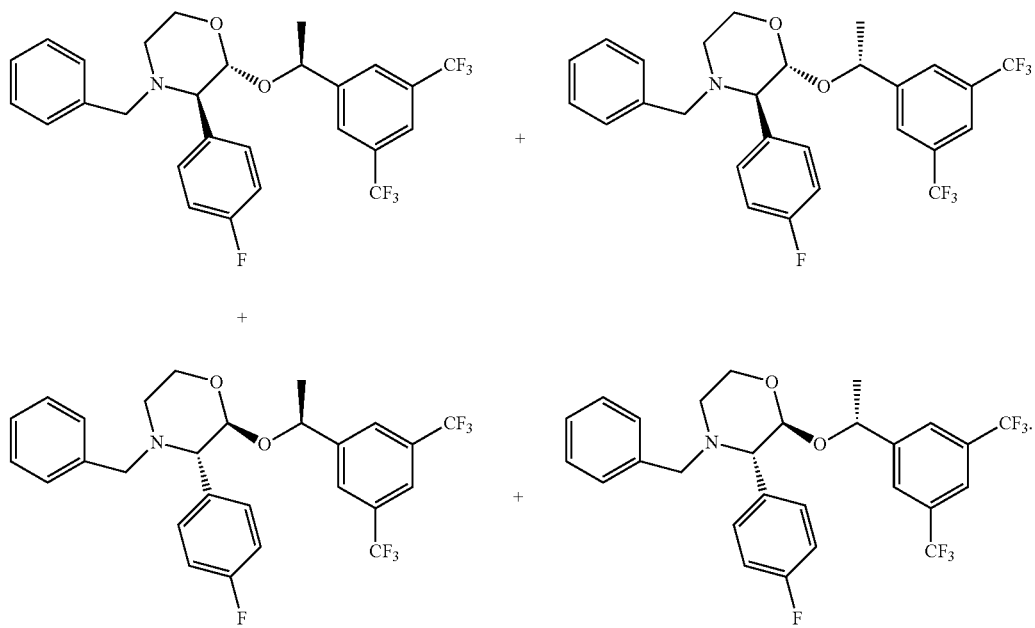

In another embodiment, the invention comprises a process for preparing aprepitant, comprising reducing a compound having the formula:

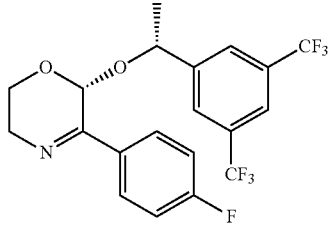

or a salt thereof, with a chemical reducing agent to form a compound having the formula:

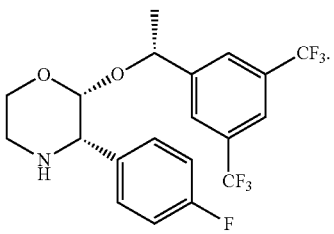

In a further embodiment, the invention comprises a compound having the formula:

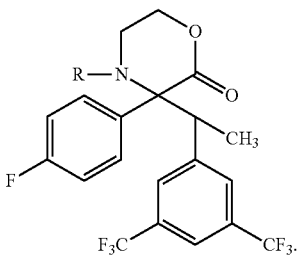

In a still further embodiment, the invention comprises a process for preparing a compound having the formula:

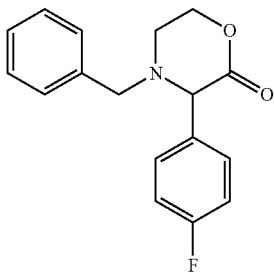

comprising hydrolyzing a compound having the formula:

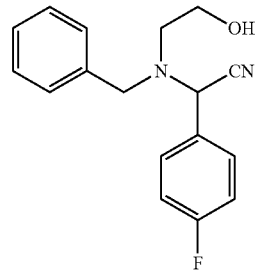

to form a compound having the formula:

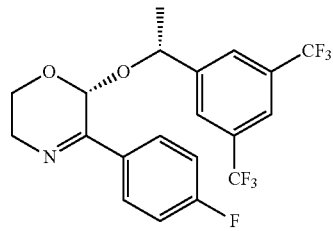

and cyclizing with an acid or base.

A yet further embodiment of the invention comprises a process for purifying a compound having the formula:

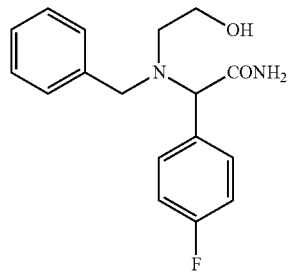

comprising crystallizing from an alcohol, dissolving in a hydrocarbon and removing solvent to form a residue, dissolving a residue in an alcohol and treating with sodium borohydride, removing an alcohol, extracting with a hydrocarbon, and forming an oxalate salt.

These and other aspects and embodiments of the invention will be described in more detail with reference to the following detailed description of the invention.

DETAILED DESCRIPTION OF THE INVENTION

Figure 1:
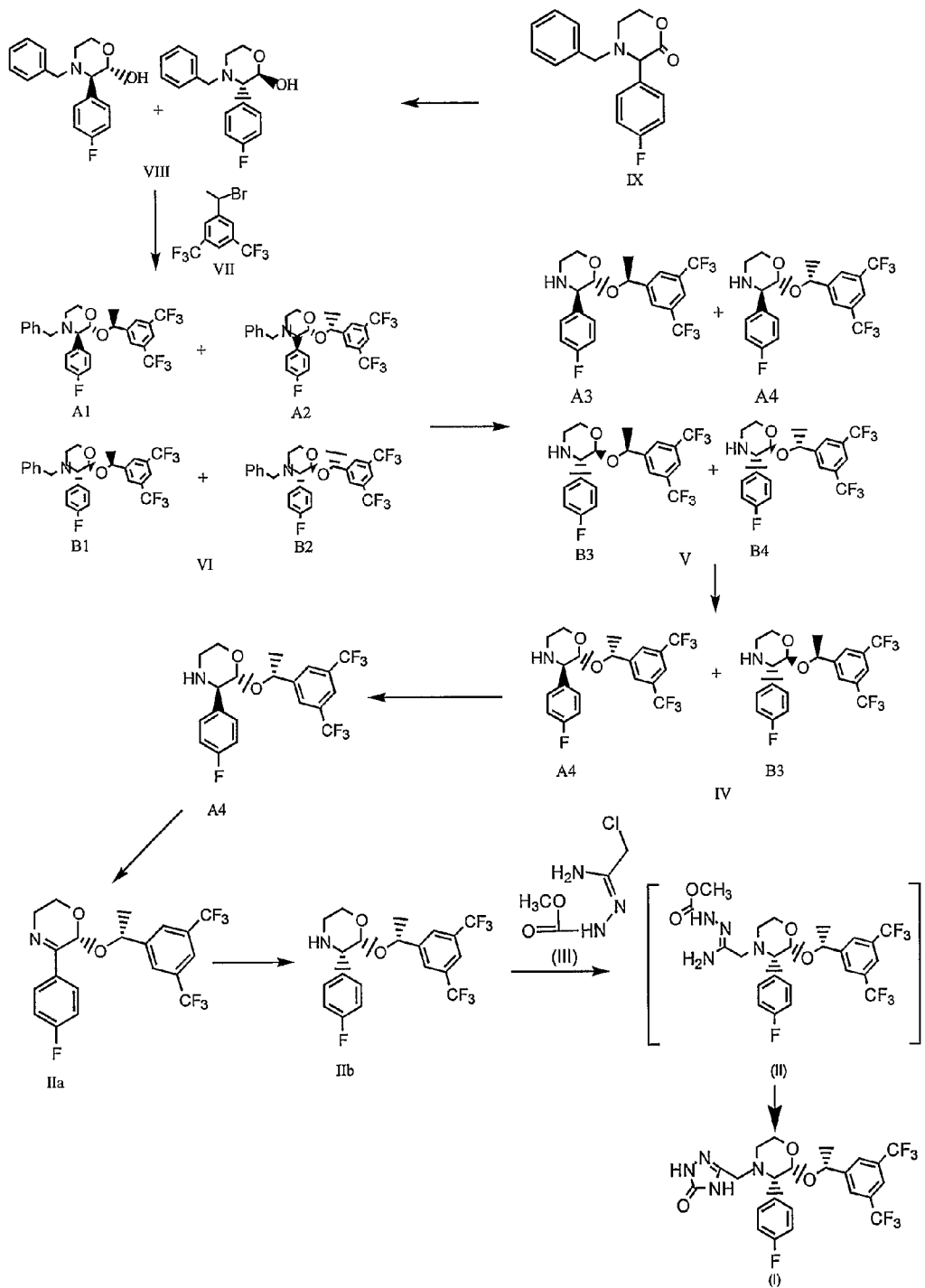
FIG. 1 is a schematic representation of a process for the synthesis of aprepitant of Formula I.

In one embodiment of the present invention, there is provided a process for the synthesis of Formula I as depicted in the reaction scheme of FIG. 1, comprising the steps of:

a) reduction of racemic intermediate compound 4-benzyl-3-(4-fluorophenyl) morpholin-2-one compound of Formula IX using suitable selective reducing agent in the presence of suitable organic solvent(s) to afford a racemic mixture of compound of Formula VIII;

b) condensation of the compound of Formula VIII with the compound of Formula VII in the presence of suitable base and organic solvent(s) to afford the racemic compound of Formula VI;

c) debenzylation of the racemic mixture of the compound of Formula VI using a suitable reducing agent in the presence of a suitable organic solvent(s) to afford the racemic mixture of the compound of Formula V;

d) diastereomeric crystallization of the compound of Formula V using suitable organic solvent(s) to afford the compound of Formula IV;

e) resolution of the compound of Formula IV using suitable chiral reagent in the presence of suitable organic solvent(s) to afford the compound of Formula A4;

f) dehydrogenation of the compound of Formula A4 using suitable dehydrogenating agents in the presence of suitable organic solvent(s) to afford the compound of Formula IIa;

g) reduction of the compound of Formula IIa using suitable reducing agent in presence of suitable organic solvent(s) to afford the compound of Formula IIb;

h) condensation of compound of Formula IIb with the compound of Formula III in the presence of suitable base and organic solvent(s) to afford the compound of Formula II; and i) cyclisation of the compound of Formula II in the presence of suitable organic solvent(s) to afford the compound of Formula I.

Step a) involves reduction of the racemic intermediate compound 4-benzyl-3-(4-fluorophenyl) morpholin-2-one of Formula IX using a suitable selective reducing agent in the presence of a suitable organic solvents to afford the racemic compound of Formula VIII.

Suitable and selective reducing agents include but are not limited to lithium tri-sec-butylborohydride ("L-selectride"), sodium borohydride, potassium borohydride, sodium hydride, sodium dihydro-bis-(2-methoxyethoxy) aluminate ("Vitride") and the like.

Suitable organic solvents include but are not limited to: alcohols such as methanol, ethanol, isopropanol, n-butanol and the like; ethers such as tetrahydrofuran (THF), diethylether, methyl tertiary-butyl ether, 1,4-dioxane and the like; aromatic hydrocarbons such as toluene, xylene, and the like; and mixtures thereof or their combinations with water in various proportions.

Suitable temperatures for conducting the reaction range from about 10° C. to about 50° C., or from about 20° C. to about 40° C.

Step b) involves condensation of the compound of Formula VIII with the compound of Formula VII in the presence of a suitable base and organic solvent to afford the racemic compound of Formula VI.

Suitable bases include but are not limited to: organic bases such as lithium diisopropylamine, n-butyl lithium, sodium tertiary-butoxide, potassium tertiary-butoxide, lithium tertiary-butoxide, N,N-diethylamine, N,N,N-triethylamine, N,N-diisopropylamine, ethyl amine, triethanolamine and the like; and inorganic bases such as sodium hydride, sodium hydroxide, potassium hydroxide, potassium carbonate, sodium carbonate, sodium bicarbonate, potassium bicarbonate, sodium methoxide, potassium methoxide, lithium methoxide and the like.

Suitable organic solvents include but are not limited to: aprotic solvents such as dimethylsulfoxide (DMSO), N,N-dimethylformamide (DMF), N-methylpyrrolidone (NMP) and the like; ketones such as acetone, methyl ethyl ketone, methyl isobutyl ketone and the like; ethers such tetrahydrofuran (THF), diethylether, methyl tertiary-butyl ether and the like; hydrocarbons such as toluene, xylene, cyclohexane and the like; alcohols such as methanol, ethanol, isopropanol; and mixtures thereof or their combinations with water in various proportions.

Surprisingly, the compound represented by Formula VI has only four optical isomers, while it would be expected to have eight. The stereospecificity of the preceding synthesis steps results in a decreased complexity when the subsequent separations of isomers are made, and also produces a higher yield of the desired final product.

Suitable temperatures for conducting the reaction range from about 10° C. to about 50° C., or from about 20° C. to about 40° C.

Step c) involves debenzylation of the racemic mixture of the compound of Formula VI using a suitable reducing agent in the presence of a suitable organic solvent to afford the racemic mixture of the compound of Formula V.

Suitable reducing agents include but are not limited to noble metal catalysts such as palladium on carbon, palladium on alumina, palladium on barium sulfate, palladium on calcium carbonate, palladium on barium carbonate, palladium on strontium carbonate, palladium hydroxide on carbon, Raney nickel, platinum oxide, and the like. Lewis acids such as boron trifluoride can also be used.

Optionally, the compound of Formula VI is contacted with a strong inorganic or organic acid prior to reduction. The acids include but are not limited to: inorganic acids such as hydrochloric acid, hydrobromic acid, sulphuric acid, phosphoric acid, formic acid, acetic acid and the like; and organic acids such as oxalic acid, tartaric acid, camphorsulphonic acid, dipara-toluoyl tartaric acid, benzene sulfonic acid, 4-toluenesulfonic acid and the like. In an embodiment, the compound of Formula VI is reacted with hydrochloric acid, and the hydrochloride salt is used for the debenzylation reaction.

Suitable organic solvents include but are not limited to: alcohols such as methanol, ethanol, n-propanol, isopropylalcohol, n-butanol, isobutylalcohol, tertiary butyl alcohol, and the like; hydrocarbons such as toluene, xylene, cyclohexane and the like; esters such as ethyl acetate, isopropyl acetate, n-butyl acetate, tertiary-butyl acetate and the like; and mixtures thereof or their combinations with water in various proportions.

Suitable temperatures for conducting the reaction range from about 10° C. to about 50° C., or from about 20° C. to about 30° C.

Step d) involves diastereomeric crystallization of the compound of Formula V using suitable a organic solvent to afford the compound of Formula IV.

Suitable organic solvents include but are not limited to: alcohols such as methanol, ethanol, Isopropanol, butanol and the like; ketones such as acetone, methyl ethyl ketone, methyl isobutyl ketone, and the like; halogenated solvents such as dichloromethane, dichloroethane, chloroform, and the like; esters such as ethyl acetate, isopropyl acetate, n-propyl acetate and the like; nitriles such as acetonitrile, propionitrile and the like; hydrocarbons such as toluene, cyclohexane, heptane, xylene and the like; and mixtures thereof or their combinations with water in various proportions.

Suitable temperatures for conducting the crystallization range from about 10° C. to about 50° C., or from about 20° C. to about 40° C.

Step e) involves resolution of the compound of Formula IV using a suitable chiral reagent in the presence of a suitable organic solvent to afford the compound of Formula A4.

Suitable chiral resolving agents include but are not limited to: tartaric acids such as di-benzoyl tartaric acids, di-p-toluoyl tartaric acids and o-nitrobenzoyl tartaric acids, and the like; camphorsulphonic acids such as 10-camphorsulphonic acid and 8-camphorsulphonic acid and the like; malic acids, N-acetyl glutamic acids, mandelic acids and the like.

Suitable organic solvents include but are not limited to: alcohols such as methanol, ethanol, isopropanol, butanol and the like; ketones such as acetone, methyl ethyl ketone, methyl isobutyl ketone, and the like; halogenated solvents such as dichloroethane, dichloromethane, chloroform and the like; esters such as ethyl acetate, isopropyl acetate, n-propyl acetate and the like; nitriles such as acetonitrile, propionitrile and the like; hydrocarbons such as toluene, xylene, cyclohexane, heptane, xylene and the like; and mixtures thereof in various proportion without limitation.

Suitable temperatures for conducting the reaction range from about 0° C. to about 75° C., or from about 25° C. to about 55° C.

Step f) involves dehydrogenation of the compound of Formula A4 using suitable dehydrogenating agents in the presence of a suitable organic solvent to afford the compound of Formula IIa.

Suitable dehydrogenating agents include but are not limited to dibromouricil (DBU) and N-chlorosuccinimide (NCS),2,3-dichloro-5,6-dicyano-1,4-benzoquinone (DDQ) and the like.

Suitable organic solvents include but are not limited to: aprotic polar solvents such as dimethylsulfoxide (DMSO), N,N-dimethylformamide (DMF), N-methylpyrrolidone (NMP) and the like; ethers such as tetrahydrofuran (THF), diethyl ether, methyl tertiary-butyl ether and the like; esters such as ethyl acetate, isopropyl acetate, n-propyl acetate and the like; nitriles such as acetonitrile, propionitrile and the like; hydrocarbons such as toluene, cyclohexane, heptane, xylene and the like; and mixtures thereof or their combinations with water in various proportions.

Suitable temperatures for conducting the reaction range from about 10° C. to about 50° C., or from about 20° C. to about 40° C.

Step g) involves reduction of the compound of Formula IIa using a suitable reducing agent in the presence of a suitable organic solvent to afford the compound of Formula IIb.

Suitable reducing agents include but are not limited to hydrogen with a palladium catalyst such as palladium on carbon, palladium on alumina, palladium on barium sulfate, palladium on calcium carbonate, palladium on barium carbonate, palladium on strontium carbonate, palladium hydroxide on carbon, and the like.

Alternatively, the reduction of the compound of Formula IIa to give the compound of Formula IIb can be accomplished using chemical reducing agents such as sodium borohydride, potassium borohydride, sodium dihydro-bis-(2-methoxyethoxy) aluminate (Vitride), sodium cyanoborohydride, sodium triacetoxyborohydride, and the like in the presence of a suitable organic solvent such as: alcohols such as methanol, ethanol, isopropanol, n-butanol, isobutyl alcohol, tertiary-butyl alcohol, and the like; hydrocarbons such as toluene, xylene, cyclohexane and the like; esters such as ethyl acetate, isopropyl acetate, n-butyl acetate, tertiary butyl acetate and the like; and mixtures thereof or their combinations with water in various proportions.

Typically, using a reducing agent such as sodium borohydride for conversion of the compound of Formula IIa to the compound of Formula IIb enhances the high purity and yield of the final compound.

Suitable organic solvents include but are not limited to: alcohols such as methanol, ethanol, isopropanol, n-butanol, isobutyl alcohol, tertiary-butyl alcohol, and the like; hydrocarbons such as toluene, xylene, cyclohexane and the like; esters such as ethyl acetate, isopropyl acetate, n-butyl acetate, tertiary butyl acetate and the like; and mixtures thereof or their combinations with water in various proportions.

Suitable temperatures for conducting the reaction range from about 10° C. to about 50° C., or from about 20° C. to about 40° C.

Step h) involves condensation of the compound of Formula IIb with the compound of Formula III in the presence of a suitable base and organic solvent to afford the compound of Formula II.

Suitable bases include, but are not limited to: organic bases such as N,N-diethylamine, triethylamine, N,N-diisopropylethylamine, triethanolamine, and the like; and inorganic bases such as sodium hydroxide, potassium hydroxide, sodium carbonate, potassium carbonate, sodium bicarbonate, potassium bicarbonate and the like.

Suitable organic solvents include, but are not limited to: aprotic polar solvents such as dimethylsulfoxide (DMSO), N,N-dimethylformamide (DMF), N-methylpyrrolidinone (NMP), and the like; ethers such as tetrahydrofuran (THF), diethyl ether, methyl tertiary-butyl ether, and the like; esters such as ethyl acetate, isopropyl acetate, n-propyl acetate, and the like; nitriles such as acetonitrile, propionitrile, and the like; hydrocarbons such as toluene, cyclohexane, heptane, xylene, and the like; and mixtures thereof or their combinations with water in various proportions.

Suitable temperatures for conducting the reaction range from about 35° C. to about 120° C., or from about 25° C. to about 110° C.

Step i) involves cyclisation of the compound of Formula II in the presence of a suitable organic solvent to afford the compound of Formula I.

Suitable organic solvents include, but are not limited to: hydrocarbons such as toluene, cyclohexane, heptane, xylene, and the like; aprotic polar solvents such as dimethylsulfoxide (DMSO), N,N-dimethylformamide (DMF), N-methylpyrrolidinone (NMP), and the like; ethers such as tetrahydrofuran (THF), diethyl ether, methyl tertiary-butyl ether, and the like; esters such as ethyl acetate, isopropyl acetate, n-propyl acetate, and the like; nitriles such as acetonitrile, propionitrile, and the like; and mixtures thereof or their combinations with water in various proportions.

Suitable temperatures for conducting the reaction range from about 35° C. to about 120° C., or from about 25° C. to about 110° C.

Figure 2:
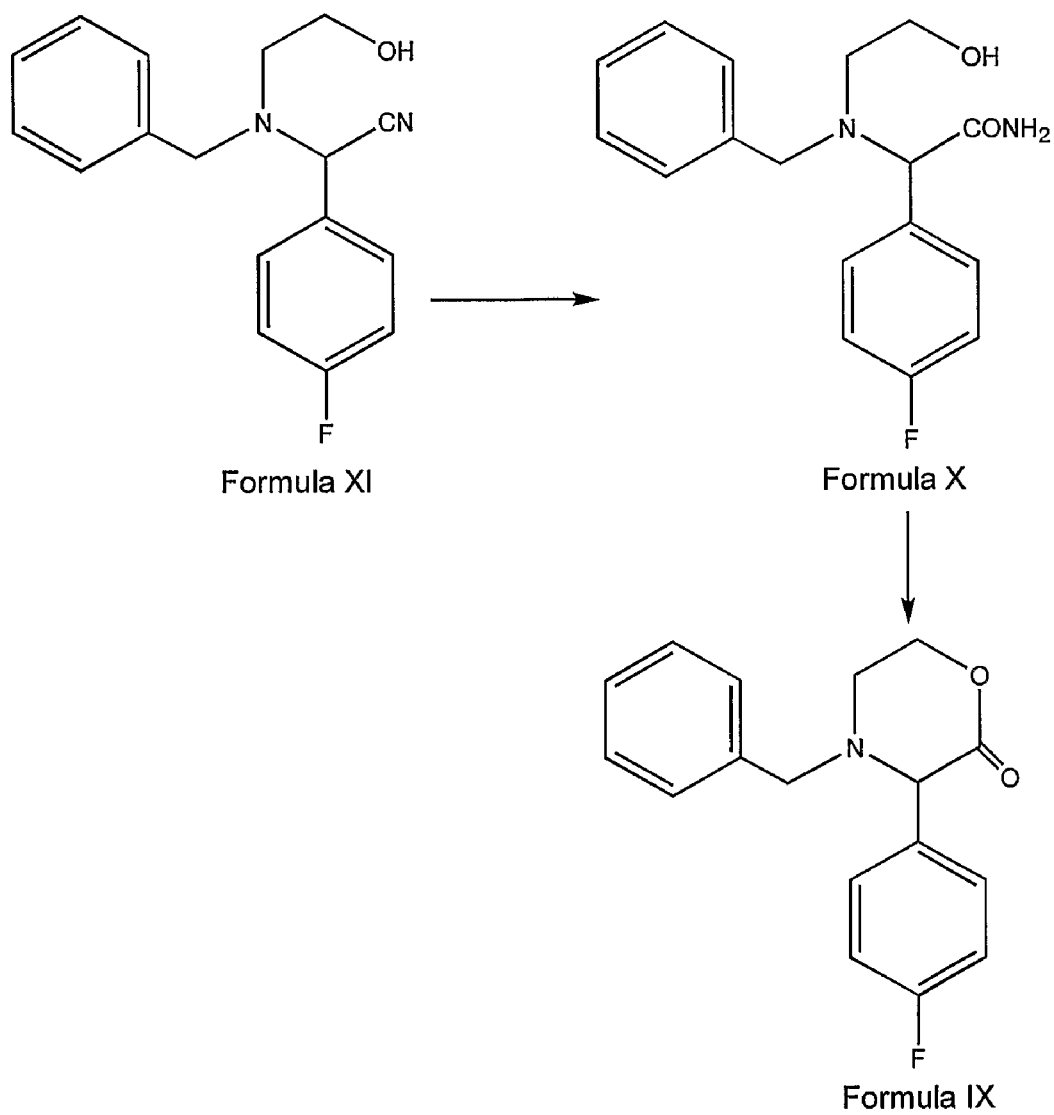
FIG. 2 is a schematic representation of a process for the synthesis of the compound having Formula IX.

In another embodiment of the present invention, there is provided a process, such as is shown in FIG. 2, for the synthesis of the compound N-benzyl-3-(4-fluorophenyl)-1,4-oxazin-2-one of Formula IX, which is an intermediate in the synthesis of aprepitant of Formula I, comprising the steps of:

a) hydrolysis of the compound [benzyl-(2-hydroxyethyl)-amino]-(4-fluorophenyl)-acetonitrile of Formula XI

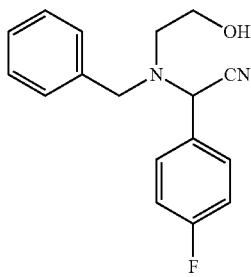

Formula XI to form the compound 2-(N-benzyl-N-(2-hydroxyethyl) amino)-2-(4-fluorophenyl) acetamide of Formula X

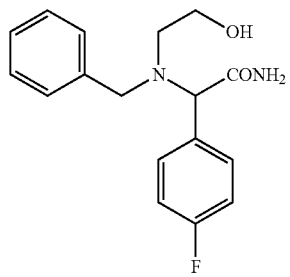

Formula X using a suitable hydrolyzing agent in the presence of a suitable base and organic solvent; and b) cyclization of the compound 2-(N-benzyl-N-(2-hydroxyethyl)amino)-2-(4-fluorophenyl) acetamide of Formula X using a suitable acid or base in the presence of a suitable organic solvent to afford the compound N-benzyl-3-(4-fluorophenyl)-1,4-oxazin-2-one of Formula IX.

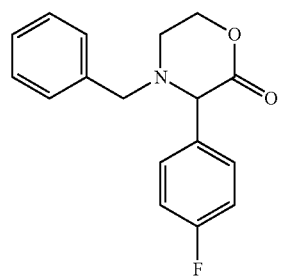

Formula IX

Step a) involves the hydrolysis of compound [Benzyl-(2-hydroxyethyl)-amino]-(4-fluorophenyl)-acetonitrile of Formula XI to form intermediate compound 2-(N-benzyl-N-(2-hydroxyethyl)amino)-2-(4-fluorophenyl) acetamide of Formula X using suitable hydrolyzing agents in the presence of a suitable base and organic solvent.

Suitable hydrolyzing agents include but are not limited to hydrogen peroxide, metachloroperoxybenzoic acid, peroxy acetic acid and the like.

Suitable organic solvents include but are not limited to aprotic polar solvents such as dimethylsulfoxide (DMSO), N,N-dimethylformamide (DMF), N,N-dimethylacetamide (DMA), tetrahydrofuran, acetone, acetonitrile, toluene and the like or mixtures thereof or their combinations with water in various proportions.

Suitable bases include, without limitation: organic bases such as methylamine, dimethylamine, triethylamine and the like; and inorganic bases such as sodium hydroxide, potassium hydroxide, sodium carbonate, potassium carbonate, sodium bicarbonate, potassium bicarbonate, sodium methoxide, potassium methoxide and the like.

Suitable temperatures for conducting the reaction range from about 10° C. to about 50° C., or from about 25° C. to about 35° C.

Step b) involves cyclization of the compound 2-(N-benzyl-N-(2-hydroxyethyl) amino)-2-(4-fluorophenyl) acetamide of Formula X using a suitable acid or base in the presence of a suitable organic solvent to afford the compound N-benzyl-3-(4-fluorophenyl)-1,4-oxazin-2-one of Formula IX.

Suitable acids include but are not limited to: methanesulfonic acid; a tartaric acid such as DL-tartaric acid, D-(−)-tartaric acid, L-(+)-tartaric acid, trifluoroacetic acid, trifluoromethanesulfonic acid; mandelic acid; camphorsulfonic acid; sulfuric acid; phosphoric acid; an arylsulfonic acid, such as benzenesulfonic acid, p-toluenesulfonic acid, and p-chlorobenzenesulfonic acid; hydrochloric acid; acetic acid; and the like.

Suitable bases include, without limitation: organic bases such as methylamine, dimethylamine, triethylamine and the like; and inorganic bases such as sodium hydroxide, potassium hydroxide, sodium carbonate, potassium carbonate, sodium bicarbonate, potassium bicarbonate, sodium methoxide, potassium methoxide and the like.

Suitable organic solvents include but are not limited to: ketones such as acetone, ethyl methyl ketone, methyl isobutyl ketone and the like; esters such as ethyl acetate, n-propyl acetate, n-butyl acetate, t-butyl acetate and the like; ether solvents such as diethyl ether, dimethyl ether, di-isopropyl ether, methyl tertiary-butyl ether, tetrahydrofuran, 1,4-dioxane and the like; hydrocarbons such as toluene, xylene and the like; nitriles such as acetonitrile, propionitrile and the like; and mixtures thereof or their combinations with water in various proportions.

Suitable temperatures for conducting the reaction range from about 0° C. to about 75° C., or from about 25° C. to about 55° C.

In a further aspect, the present invention provides the compound of Formula X.

The reaction temperatures can range from about 50° C. to about 139° C. for the conversion of the compound of Formula II to the compound of Formula I.

The compound of Formula II of FIG. 1 can be used for subsequent reactions as prepared in situ, or can optionally be isolated prior to further reaction.

In yet another embodiment of the present invention, there is provided a purification process for aprepitant of Formula I comprising the steps of:

a) dissolving aprepitant in a suitable organic solvent at elevated temperatures;

b) cooling the solution of step a) to about 0-35° C.;

c) separating the solid precipitated in step b);

d) washing the solid obtained in step c) with the solvent used in the step a); and e) drying the solid obtained in step d) at about 25-100° C. to afford the desired purity of the compound of Formula I.

In yet further embodiment of the present invention, there is provided a potential spiro impurity of aprepitant having Formula IIc.

Figure 3:
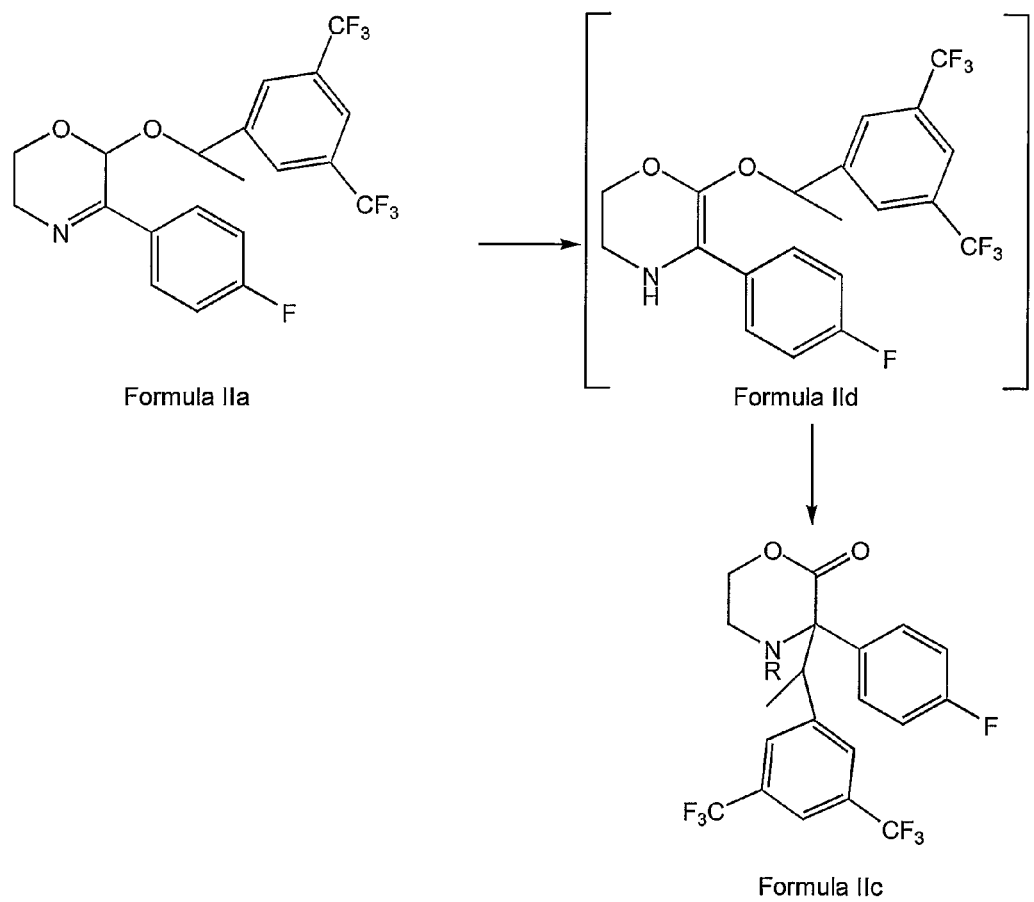
FIG. 3 is a schematic representation of a synthesis of the spiro impurity of Formula IIc.

In yet another embodiment of the present invention there is provided a process, such as is shown in FIG. 3, for the preparation of the spiro impurity of Formula IIc comprising the steps of:

i) providing a solution of (6R-6-{(1R)-1-[3,5-bis(trifluoromethyl)-phenyl]ethoxy}-5-(4-fluorophenyl)-3,6-dihydro-2H-[1,4]oxazine) of Formula IIa in a suitable organic solvent;

ii) distilling the solvent from the solution of step i) under reduced pressure;

iii) suspending the residue obtained in step ii) in a suitable organic solvent; and iv) separating the compound having Formula IIc.

Suitable organic solvents that can be used in an embodiment include but are not limited to alcohols such as methanol, ethanol, isopropyl alcohol, n-propanol, n-butanol, tertiary butylalcohol, and the like; ketonic solvents such as acetone, ethylmethyl ketone, methyl isobutyl ketone and the like; esters such as ethyl acetate, n-propyl acetate, n-butyl acetate, t-butyl acetate and the like; ether solvents such as diethyl ether, dimethylether, di-isopropylether, methyltertiarybutyl ether, tetrahydrofuran, 1,4-dioxane and the like; hydrocarbon solvents such as toluene, xylene, petroleum ether, n-hexane, n-heptane, cyclohexane and the like; nitrile solvents such as acetonitrile, propionitrile and the like; aprotic polar solvents such as N,N-dimethyl formamide (DMF), Dimethylsulfoxide (DMSO), N,N-dimethylacetamide (DMA) and the like; or mixtures of any two or more thereof or their combination with water in various proportions.

Suitable temperatures for conducting the reaction range from about 35° C. to about 100° C., or from about 25° C. to about 95° C.

The potential spiro impurity is formed during the synthesis of 6R-6-{(1R)-1-[3,5-(trifluoromethyl) phenyl]ethoxy}-5-(4-fluorophenyl)-3,6-dihydro-2H-[1,4]oxazine of Formula IIa by sigmatropic rearrangement of the compound of Formula IIa. This spiro impurity is identified with reference to its 0.95 relative retention time (RRT) by the HPLC analytical method.

The temperature(s) for the dissolution of aprepitant of Formula I can range from about 25° C. to the reflux temperature of the solvent used.

The temperature(s) for the precipitation of the compounds of Formula I and Formula II can range from about 0° C. to about 35° C.

The drying temperature(s) for the drying the compounds of Formula I and Formula II can range from about 25° C. to about 100° C.

The solvent can be removed from the solution using distillation with or without vacuum, spray drying, or agitated thin film drying. The solvent can also be removed from the solution using other techniques known in art including, for example, distillation, evaporation, oven drying, tray drying, rotational drying (such as with the Buchi Rotavapor), freeze-drying, fluidized bed drying, flash drying, spin flash drying, and the like.

The process may include optionally further drying of the product obtained from the solution by known drying methods useful in the practice of the present invention will be apparent to the skilled artisan.

As used herein, the term "reference standard" refers to a compound that may be used both for quantitative and qualitative analysis of an active pharmaceutical ingredient. For example, the HPLC or GC retention time of the compound allows a relative retention time to be determined, thus making qualitative analysis possible. The concentration of the compound in solution before injection into an HPLC or GC column allows the areas under the HPLC or GC peaks to be compared, thus making quantitative analysis possible.

Reference standards are described in general terms above. However, as will be understood by those skilled in the art, a detector response can be, for example, the peak heights or integrated peak areas of a chromatogram obtained, e.g., by UV or refractive index detection, from the eluent of an HPLC system or, e.g., flame ionization detection (FID) or thermal conductivity detection, from the eluent of a gas chromatograph, or other detector response, e.g., the UV absorbance of spots on a fluorescent TLC plate. The position of the reference standard may be used to calculate the relative retention time for aprepitant and impurities of aprepitant.

As used herein, the term "substantially", in reference to relative retention times (RRTs) being substantially the same, refers to a relative standard deviation that is equal to or less than 5% for a population of 6 injections.

An aspect of the present invention is directed to an impurity of aprepitant, which was previously unidentified, its preparation as well as of other known impurities, and to the use of this impurity as reference standard for the analytical quantification of aprepitant purity, as required in the manufacture of high purity aprepitant.

Figure 4:
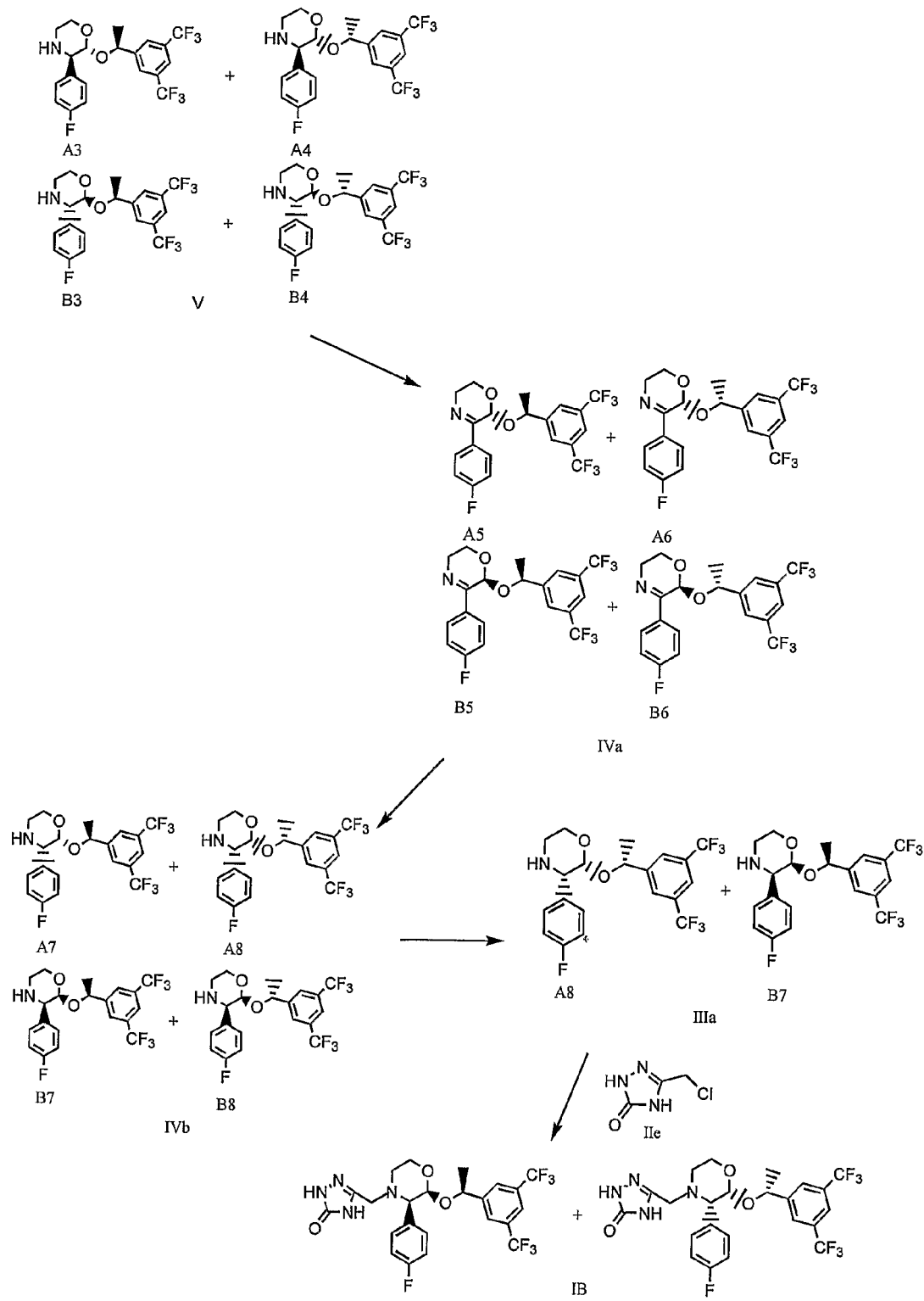
FIG. 4 is a diagram of a process scheme for preparing racemic aprepitant.

In another embodiment of the present invention there is provided a process for the synthesis of racemic aprepitant of Formula IB as depicted in the process scheme of FIG. 4, which is a useful intermediate in the preparation of aprepitant of Formula I, comprising the steps of:

i) dehydrogenation of the compound of Formula V of FIG. 1 to an imine compound of Formula IVa using a suitable dehydrogenating agent in the presence of a suitable organic solvent;

ii) reduction of the imine compound of Formula IVa to the amine compound of Formula IVb using a suitable reducing agent in the presence of a suitable solvent;

iii) diastereomeric crystallization of the amine compound of Formula IVb to afford the desired enantiomeric mixture compound of Formula IIIa using a suitable organic solvent; and iv) condensation of the compound of Formula IIIa with the compound 3-halomethyl-1,2,4-triazolin-5-one of Formula IIe to give racemic aprepitant of Formula IB using a suitable base in the presence of a suitable solvent.

Step i) involves dehydrogenation of the compound of Formula V to an imine compound of Formula IVa using a suitable dehydrogenating agent in the presence of a suitable organic solvent.

Suitable dehydrogenating-agents include but are not limited to dibromouricil (DBU), N-chlorosuccinimide (NCS),2,3-dichloro-5,6-dicyano-1,4-benzoquinone (DDQ) and the like.

Suitable organic solvents include but are not limited to: aprotic polar solvents such as dimethylsulfoxide (DMSO), N,N-dimethylformamide (DMF), N-methylpyrrolidone (NMP) and the like; ethers such as tetrahydrofuran (THF), diethylether, methyl tertiary-butyl ether and the like; esters such as ethyl acetate, isopropyl acetate, n-propyl acetate and the like; nitriles such as acetonitrile, propionitrile and the like; hydrocarbons such as toluene, cyclohexane, heptane, xylene and the like; and mixtures thereof or their combinations with water in various proportions.

Suitable temperatures for conducting the reaction range from about 0° C. to about 25° C., or from about 10° C. to about 35° C.

Step ii) involves reduction of the imine compound of Formula IVa to the amine compound of Formula IVb using a suitable reducing agent in the presence of a suitable organic solvent.

Suitable reducing agents include but are not limited to noble metal catalysts such as palladium on carbon, palladium on alumina, palladium on barium sulfate, palladium on calcium carbonate, palladium on barium carbonate, palladium on strontium carbonate, palladium hydroxide on carbon and the like.

Suitable organic solvents include but are not limited to: alcohols such as methanol, ethanol, n-propanol, isopropyl alcohol, n-butanol, tertiary butyl alcohol and the like; hydrocarbons such as toluene, xylene, cyclohexane and the like; esters such as ethyl acetate, methyl acetate, isopropyl acetate and the like; and mixtures thereof or their combinations with water in various proportions.

Suitable temperatures for conducting the reaction range from about 35° C. to about 75° C., or from about 25° C. to about 50° C.

Step iii) involves diastereomeric crystallization of the amine compound of Formula IVb to afford the desired enantiomeric mixture compound of Formula IIIa using a suitable organic solvent.

Suitable organic solvents include but are not limited to: water, alcohols such as methanol, ethanol, isopropanol, butanol and the like; ketones such as acetone, methyl ethyl ketone, methyl isobutyl ketone and the like; halogenated solvents such as dichloroethane, dichloromethane, or chloroform, esters such as ethyl acetate, isopropyl acetate, n-propyl acetate and the like; nitriles such as acetonitrile, propionitrile and the like; hydrocarbons such as toluene, cyclohexane, heptane, xylene and the like; and mixtures thereof.

Suitable temperatures for conducting the reaction range from about 0° C. to about 50° C., or from about 10° C. to about 40° C.

Step iv) involves condensation of the compound of Formula IIIa with the compound 3-halomethyl-1,2,4-triazolin-5-one of Formula IIe (showing the halo substituent as being chloro) to give racemic aprepitant of Formula IB using a suitable base in the presence of a suitable organic solvent. The halo substituent can also be bromo or iodo.

Suitable bases include but are not limited to: organic bases such as N,N-diethylamine, triethylamine, N,N-diisopropylamine, ethyl amine, triethanolamine and the like; and inorganic bases such as sodium hydride, sodium hydroxide, potassium hydroxide, potassium carbonate, sodium carbonate, sodium bicarbonate, potassium bicarbonate and the like.

Suitable organic solvents include but are not limited to: aprotic polar solvents such as dimethylsulfoxide (DMSO), N,N-dimethylformamide (DMF), N-methylpyrrolidone (NMP) and the like; ethers such as tetrahydrofuran, diethylether, methyl tertiary-butyl ether and the like; esters such as ethyl acetate, isopropyl acetate, n-propyl acetate and the like; nitriles such as acetonitrile, propionitrile and the like; hydrocarbons such as toluene, cyclohexane, heptane, xylene and the like; and mixtures thereof or their combinations with water in various proportions.

Suitable temperatures for conducting the reaction range from about 10° C. to about 25° C., or from about 0° C. to about 5° C.

Figure 5:
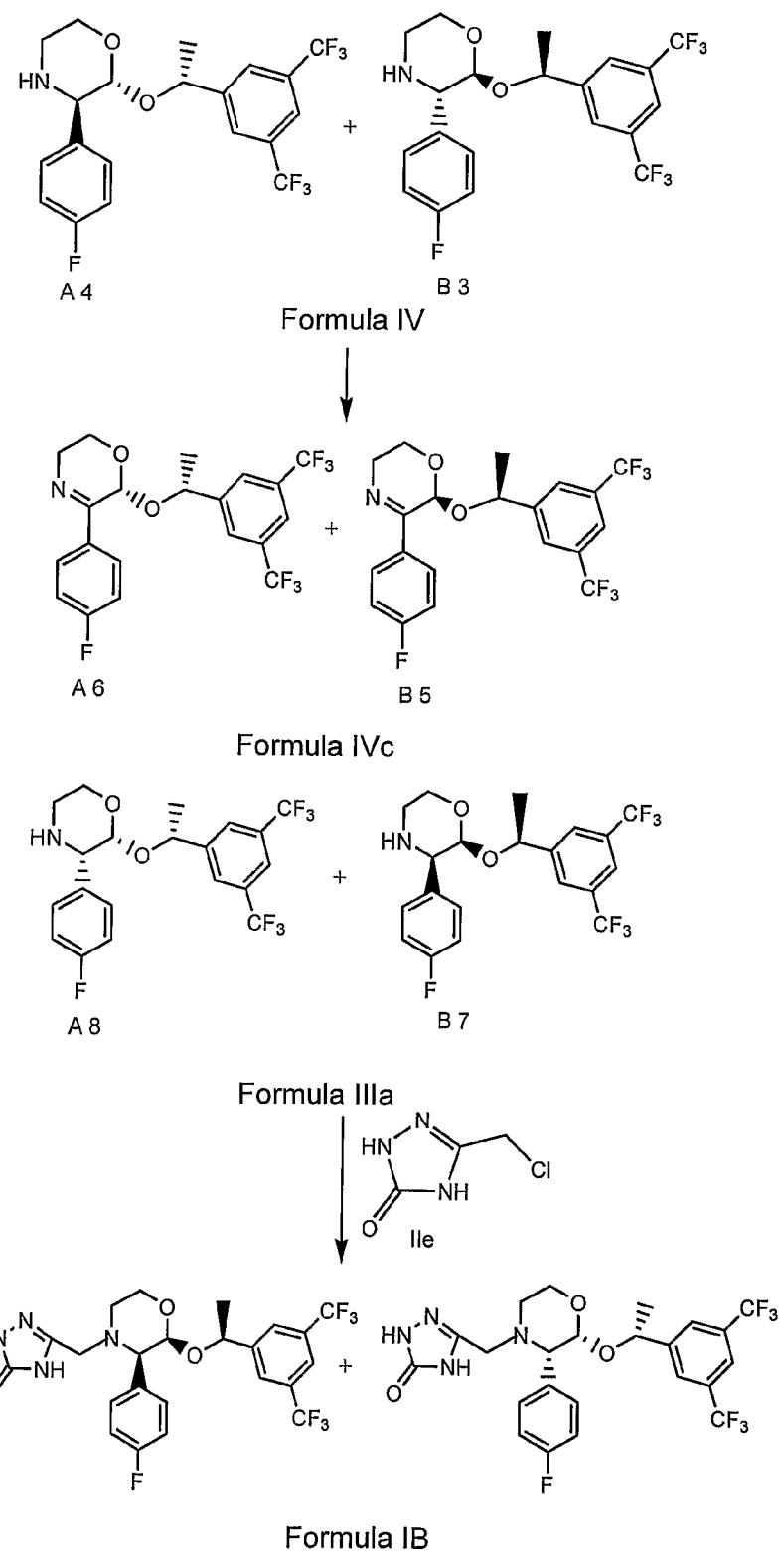
FIG. 5 is a diagram of a process scheme for preparing racemic aprepitant.

In yet another embodiment of the present invention, there is provided an alternative process for the synthesis of the racemic aprepitant compound of Formula IB, which is a useful intermediate in the preparation of aprepitant of Formula I, as outlined by the process scheme of FIG. 5, comprising the steps of:

A) dehydrogenation of the compound of Formula IV to afford the imine compound of Formula IVc using a suitable dehydrogenating agent in the presence of a suitable organic solvent;

B) reduction of the imine compound of Formula IVc to afford the amine compound of Formula IIIa using a suitable reducing agent in the presence of a suitable organic solvent; and C) condensation of the amine compound of Formula IIIa with the compound 3-chloromethyl-1,2,4-triazolin-5-one of Formula IIe to afford the racemic aprepitant of Formula IB using a suitable base in the presence of a suitable organic solvent.

Step A) involves dehydrogenation of the compound of Formula IV to afford the imine compound of Formula IVc using a suitable dehydrogenating agent in the presence of a suitable organic solvent.

Suitable dehydrogenating agents include but are not limited to dibromouricil (DBU), N-chlorosuccinimide (NCS),2,3-dichloro-5,6-dicyano-1,4-benzoquinone (DDQ) and the like.

Suitable organic solvents include but are not limited to: aprotic polar solvents such as dimethylsulfoxide (DMSO), N,N-dimethylformamide (DMF), N-methylpyrrolidone (NMP) and the like; ethers such as tetrahydrofuran (THF), diethyl ether, methyl tertiary-butyl ether and the like; esters such as ethyl acetate, isopropyl acetate, n-propyl acetate and the like; nitriles such as acetonitrile, propionitrile and the like; hydrocarbons such as toluene, cyclohexane, heptane, xylene and the like; and mixtures thereof or their combinations with water in various proportions.

Suitable temperatures for conducting the reaction range from about 10° C. to about 25° C., or from about 0° C. to about 5° C.

Step B) involves reduction of the imine compound of Formula IVc to afford the amine compound of Formula IIIa using a suitable a suitable reducing agent in the presence of a suitable organic solvent.

Suitable reducing agents include but are not limited to palladium catalysts such as palladium on carbon, palladium on alumina, palladium on barium sulfate, palladium on calcium carbonate, palladium on barium carbonate, palladium on strontium carbonate, palladium hydroxide on carbon and the like.

Suitable organic solvents include but are not limited to: alcohols such as methanol, ethanol, isopropyl alcohol and the like; hydrocarbons such as toluene, xylene, cyclohexane and the like; esters such as ethyl acetate, methyl acetate, isopropyl acetate and the like; and mixtures thereof or their combinations with water in various proportions.

Suitable temperatures for conducting the reaction range from about 20° C. to about 50° C., or from about 25° C. to about 35° C.

Step C) involves condensation of the amine compound of Formula IIIa with the compound 3-chloromethyl-1,2,4-triazolin-5-one of Formula IIe to afford the racemic aprepitant of Formula IB using a suitable base in the presence of a suitable organic solvent.

Suitable bases include but are not limited to: organic bases such as N,N-diethylamine, triethylamine, N,N-diisopropylamine, ethylamine, triethanolamine and the like; and inorganic bases such as sodium hydride, sodium hydroxide, potassium hydroxide, potassium carbonate, sodium carbonate, sodium bicarbonate, potassium carbonate and the like.

Suitable organic solvents include but are not limited to: aprotic polar solvents such as dimethylsulfoxide (DMSO), N,N-dimethylformamide (DMF), N-methylpyrrolidone (NMP) and the like; ethers such as tetrahydrofuran, diethyl ether, methyl tertiary-butyl ether and the like; esters such as ethyl acetate, isopropyl acetate, n-propyl acetate and the like; nitriles such as acetonitrile, propionitrile and the like; hydrocarbons such as toluene, cyclohexane, heptane, xylene and the like; and mixtures thereof or their combinations with water in various proportions.

Suitable temperatures for conducting the reaction range from about 0° C. to about 25° C., or from about 20° C. to about 40° C.

The compound of Formula IB obtained by using different starting compounds is useful as intermediate in the preparation of aprepitant of Formula I.

The cis- and trans-morpholine acetal compounds can be readily distinguished by conventional analytical techniques such as high performance liquid chromatography ("HPLC") and nuclear magnetic resonance ("NMR") spectroscopy. The optical activities of the known compounds are well in agreement with those reported in the art.

The compound of Formula IV is separated by diastereomeric crystallization of the compound of Formula V by using suitable organic solvents under suitable conditions as described in examples.

The compound of Formula V is used in the form of any salt or directly converted to compound of Formula IV by crystallizations.

The aprepitant of Formula I obtained may be optionally purified by recrystallization or slurrying in suitable organic solvents.

Recrystallization involves providing a concentrated solution of aprepitant in a suitable solvent and then crystallizing the solid from the solution.

Suitable solvents in which aprepitant can be dissolved for purification include but are not limited to: $C_1$-$C_5$ ketones such as acetone, ethyl methyl ketone, butanone, methylisobutylketone and the like; alcohols such as ethanol, methanol, and isopropanol; ethers such as such as tetrahydrofuran, 1,4-dioxane, ethyl acetate and the like; water; and mixtures thereof in various proportions without limitation.

Suitable concentrations of the aprepitant in the solvent can range from 40 to 80% or more. The solution can be prepared at an elevated temperature if desired to achieve a higher solute concentration. Any temperature is acceptable for the dissolution as long as a clear solution of the aprepitant is obtained and is not detrimental to the drug substance chemically or physically. The solution may be brought down to a lower temperature for further processing if required or an elevated temperature may be used. A higher temperature for dissolution will allow the precipitation from solutions with higher concentrations of aprepitant, resulting in better economics of manufacture.

Suitable temperatures for dissolution the reaction range from about 0° C. to about 50° C. or reflux, or from about 20° C. to about 40° C.

The solid compound of Formula I thus obtained is recovered from the reaction mixture by suitable techniques such as for example decantation, filtration by gravity or by suction, centrifugation, and the like. Other techniques for separating the solids from the reaction mixtures are also within the scope of this invention.

The product may optionally be further dried. Drying can be suitably carried out in a tray dryer, vacuum oven, air oven, fluidized bed drier, spin flash dryer, flash dryer and the like. The drying can be carried out at temperatures of about 25° C. to about 75° C. with or without application of a vacuum and in the presence or absence of an inert atmosphere such as nitrogen, neon, argon, or helium. The drying can be carried out for any desired time periods to achieve the desired product purity, times from about 1 to 20 hours frequently being adequate.

The aprepitant of Formula I is substantially free from impurities either process, structural, and isomeric impurities. Typically the aprepitant is of high purity, such as at least 99.5 wt %, or at least 99.9 wt % purity. Correspondingly, the level of impurities may be less than about 0.5 wt %, or 0.1 wt % by high performance liquid chromatography (HPLC).

Similarly, the aprepitant of Formula I is substantially free from residual solvents such as solvents used in making the aprepitant. The residual solvent content may be less than about 10 wt %, or less than about 2 wt %, or less than about 1 wt %, about 0.5 wt %, or about 0.1 wt %, as determined by high performance liquid chromatography (HPLC).

Still another aspect of the present invention provides pharmaceutical compositions containing a therapeutically effective amount of pure aprepitant along with one or more pharmaceutically acceptable ingredients such as carriers, excipients or diluents, The pharmaceutical composition comprising aprepitant produced by the process of the invention along with one or more pharmaceutically acceptable ingredients may further formulated as: solid oral dosage forms such as, but not limited to, powders, granules, pellets, tablets, and capsules; liquid oral dosage forms such as but not limited to syrups, suspensions, dispersions, and emulsions; and injectable preparations such as but not limited to solutions, dispersions, and freeze dried compositions. Formulations may be in the form of immediate release, delayed release or modified release. Further, immediate release compositions may be conventional, dispersible, chewable, mouth dissolving, or flash melt preparations, and modified release compositions that may comprise hydrophilic or hydrophobic, or combinations of hydrophilic and hydrophobic, release rate controlling substances to form matrix or reservoir systems or combinations of matrix and reservoir systems. The compositions may be prepared by direct blending, dry granulation or wet granulation or by extrusion and spheronization. Compositions may be presented as uncoated, film coated, sugar coated, powder coated, enteric coated or modified release coated. Compositions of the present invention may further comprise one or more pharmaceutically acceptable excipients.

Pharmaceutically acceptable excipients that find use in the present invention include, but are not limited to: diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, polyvinylpyrrolidone, hydroxypropyl cellulose, hydroxypropyl methylcellulose, pregelatinized starch and the like; disintegrants such as starch, sodium starch glycolate, pregelatinized starch, crospovidone, croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants; complex forming agents such as various grades of cyclodextrins, resins; release rate controlling agents such as hydroxypropyl cellulose, hydroxymethyl cellulose, hydroxypropyl methylcellulose, ethyl cellulose, methylcellulose, various grades of methyl methacrylates, waxes and the like. Other pharmaceutically acceptable excipients that are of use include but are not limited to film formers, plasticizers, colorants, flavoring agents, sweeteners, viscosity enhancers, preservatives, antioxidants and the like.

The process of the present invention is simple, cost effective, eco-friendly, commercially suitable, and reproducible on an industrial scale.

Certain specific aspects and embodiments of the present invention will be explained in more detail with reference to the following examples, which are provided by way of illustration only and should not be construed as limiting the scope of the invention in any manner.

Example 1

Preparation of (±)-Trans-N-Benzyl-3-(4-Fluorophenyl)-1,4-Oxazin-2-Ol (Formula VIII)

500 g of N-benzyl-3-(4-fluorophenyl)-1,4-oxazin-2-one of Formula IX and 5 L of toluene were charged into a clean and dry 4 neck round bottom flask and the contents were stirred for about 15 minutes. Resultant solution was cooled to about −30° C. followed by addition of 5 L of 1M lithium tri-sec-butylborohydride ("L-selectride") (950 g in 4050 ml of tetrahydrofuran) over about 30 minutes. The reaction mixture was stirred at about −25° C. for about 1 hour. After the completion of the reaction, the reaction solution was allowed to attain a temperature of about 10° C. The reaction mixture was quenched by the addition of 2 L of 40% aqueous sodium bicarbonate solution over about 30 minutes. Organic and aqueous phases were separated and the aqueous phase was extracted with 1 L of toluene followed by separation of organic and aqueous phases. Combined organic layers were extracted with an 8% v/v aqueous hydrochloric acid solution and the resulting acidic aqueous phases were made basic with 2 L of 40% w/v ageous sodium hydroxide solution. The resultant basic solution was extracted with 2×2.5 L of toluene. The organic phases were combined and washed with 2×2.5 L of water followed by separation of organic and aqueous phases. Organic phase was distilled completely at about 75° C. to afford 392 g of the title compound.

Specific optical rotation (SOR) $[\alpha]_D^{25}=0.00°$ (C=1% MeOH);

Purity by chiral HPLC: (+)-trans isomer: 45.94%, (−)-trans isomer: 47.20%.

Example 2

Preparation of (±)-Trans-4-Benzyl-2-[2-(3,5-Bis-Trifluoro Methylphenyl)Ethoxy]-3-(4-Fluorophenyl) Morpholine (Formula VI)

250 g of the compound of Formula VIII obtained from Example 1, 280 g of 1-(1-bromoethyl)-3,5-bis-trifluoromethyl-benzene of Formula VII and 2.5 L of N,N-dimethylformamide (DMF) were charged into a clean and dry 4neck round bottom flask followed by stirring for about 15 minutes. 35 g of sodium hydroxide was charged followed by heating to about 70° C. for about 2 hours. After completion of the reaction, the reaction mass was cooled to about 30° C. followed by treating with mixture of 2.5 L of water and 1250 ml of toluene. The organic layer was separated and the resultant aqueous phase was extracted with 1250 ml of toluene. Organic and aqueous layers were separated and both the organic layers were combined. The total organic layer was washed with 2×2.5 L of water followed by separation of organic and aqueous layers. Organic layer was distilled completely at about 80° C. to afford 382 g of the title compound.

Specific optical rotation (SOR) $[\alpha]_D^{25}=0.00°$ (C=1% MeOH).

Example 3

Preparation of Paratoluenesulfonic Acid Salt of (±)-Trans-2-[1-(3,5-Bis-Trifluoromethylphenyl)Ethoxyl-3-(4-Fluorophenyl)-Morpholine (Formula IV)

300 g of the compound of Formula VI obtained from Example 2, 600 ml of methanol, 108.1 g of para-toluenesulfonic acid, 2.4 L of toluene and 300 g of 5% w/w palladium supported on carbon were charged in a clean and dry autoclave vessel. 3.5 kg/cm² of dry hydrogen gas was passed into the reaction suspension at about 30° C. and maintained over a period of about 4 hours. After completion of the reaction, the reaction mass was filtered on celite and the celite was washed with 600 ml of methanol. The resultant filtrate was distilled completely at about 60° C. under vacuum to afford 350 g of compound of Formula V. The obtained compound was slurried in 3 L of acetonitrile at 30° C. for about 2 hours followed by filtration of the solid and the solid was washed with 600 ml of acetonitrile to afford 120 g of the desired title diastereomer salt.

Specific optical rotation (SOR) $[\alpha]_D^{25}=0.00°$ (C=1% MeOH);

Purity by RS HPLC: $A_4B_3$ at RT 17.79 minutes: 96.93%; $A_3B_4$ at RT 19.9 minutes: 1.91%.

Example 4

Alternative Process for the Preparation of 2-(R)-(1-(R)-3,5-Bis(Trifluoromethyl)-Phenyl)Ethoxy-3-(S)-(4-Fluorophenyl)Morpholine (Formula IV)

5 g of 6-[1(S)-3,5-bis(trifluoromethylphenyl)ethoxy]-5-(4-fluorophenyl)-3,6-dihydro-2H-[1,4]oxazine of Formula V, and 35 ml of methanol were charged into a clean and dry round bottom flask followed by stirring for about 5-10 minutes. The resultant solution was cooled to about 0-5° C. followed by charging of 0.45 g of sodium borohydride. The solution was allowed to attain a temperature of about 25-35° C. under stirring over about 25-45 minutes. After completion of the reaction, solvent from the reaction mixture was distilled completely at about 60-65° C. followed by charging 100 ml of an equal volume mixture of water and dichloromethane. Organic and aqueous layers were separated and the aqueous layer was extracted with 25 ml of dichloromethane. Organic and aqueous layers were separated and both the organic layers were combined followed by washing with 2×50 ml of water. Organic and aqueous layers were separated and the solvent was distilled completely from the organic layer at about 35-40° C. to afford 5 g of the title compound in the form of a syrup.

$[\alpha]_D=(+75.37°)$ (C=0.6% MeOH),
RS HPLC Purity: 96.32%.

Example 5

Preparation of (2R,3R)-2-{(1R)-1-[(3,5-Bis-Trifluoromethylphenyl)Ethoxy}-3-(4-Fluorophenyl)-Morpholine (Formula A4)

100 g of the compound of Formula IV obtained from Example 3, 1500 ml of toluene and 500 ml of saturated sodium carbonate solution were charged into a clean and dry 4 neck round bottom flask followed by stirring for about 10 minutes. Organic and aqueous layers were separated and the organic layer was washed with 2×500 ml of saturated sodium carbonate solution. The organic and aqueous layers were separated and the organic layer was washed with 3×500 ml of water. Organic and aqueous layers were separated and organic layer was dried over 20 g of anhydrous sodium sulphate. Organic layer was distilled completely at about 80° C. under vacuum to afford 65 g of freebase. The obtained free base was dissolved in 260 ml of methanol, a solution of 37.3 g of L-(−)-camphor-10-sulphonic acid dissolved in 195 ml of methanol was charged, and the resultant reaction solution was stirred at about 30° C. for about 3 hours. The filtered solid, 675 ml of toluene and 225 ml of sodium carbonate solution were charged into a clean and dry round bottom flask solid, and stirred for about 20 minutes. Organic layer was separated and washed with 225 ml of 5% sodium carbonate solution and 3×225 ml of water. Organic layer was dried over 20 g of anhydrous sodium sulphate and distilled completely at about 55° C. under vacuum to afford 28.5 g of the title compound in the form of syrup.

Specific optical rotation (SOR) $[\alpha]_D^{25}$=+27.50° (C=1% MeOH);

Purity by chiral HPLC: 100%.

Example 6

Preparation of 6R-6-{(1R)-1-[3,5-Bis(Trifluoromethyl)-Phenyl]Ethoxy}-5-(4-Fluorophenyl)-3,6-Dihydro-2H-[1,4]Oxazine (Formula IIa)

28 g of the compound of Formula A4 obtained from Example 4 and 168 ml of N,N-dimethylformamide (DMF) were charged into a clean and dry 4neck round bottom flask followed by stirring for about 5 minutes. To the resulting solution 2.5 g of potassium carbonate was charged and the mass was cooled to about 0-5° C. 11.1 g of N-chlorosuccinamide was charged in small portions over about 20 minutes and the resultant reaction mass was stirred for about 30 minutes followed by addition of 16.42 g of 1,8-diazabicyclo-[5.4.0]-undec-7-ene (DBU) over about 10 minutes. The reaction mass was allowed to reach 30° C. and was stirred for about 3 hours. After completion of the reaction, 280 ml of water and 280 ml of toluene were charged under stirring followed by separation of organic and aqueous layers. The aqueous layer was extracted with 2×140 ml of toluene followed by separation of organic and aqueous layers. Both the organic layers were combined washed with 3×140 ml of water. The organic layer was dried over 20 g of anhydrous sodium sulphate and the organic layer was distilled completely under vacuum to afford 23 g of the title compound.

Example 7

Preparation of (2R,3S)-2-{(1R)-1-[3,5-Bis-Trifluoromethylphenyl]Ethoxy}-3-(4-Fluorophenyl) Morpholine (Formula IIb)

20 g of the compound of Formula IIa obtained from Example 5, 20 g of 5% w/w palladium on carbon and 200 ml of methanol were charged into a clean and dry autoclave vessel. 3.2 kg/cm² of dry hydrogen gas pressure was passed into the reaction suspension at about 30° C. for about 3 hours. After the completion of the reaction, the reaction suspension was filtered through celite and the celite was washed with 50 ml of methanol. The resultant filtrate was distilled completely at about 60° C. under vacuum to afford 18 g of the title compound.

Specific optical rotation (SOR) $[\alpha]_D^{25}$=+65.55° (C=1% MeOH).

Example 8

Preparation of Aprepitant (Formula I)

2 g of the compound of Formula IIb and 10 ml of N,N-dimethylformamide (DMF) were charged into a clean and dry 4 neck round bottom flask followed by stirring for about 5 minutes. To the resultant solution 0.69 g of potassium carbonate and 2 ml of water were charged followed by cooling to about 0° C. A solution of 0.83 g of N-methylcarboxy-2-chloroacetamidarazone of Formula III dissolved in 5.0 ml of N,N-dimethylformamide (DMF) was charged to the above mixture followed by stirring at about 5° C. for about 3 hours. After completion of the reaction, a 1:1 mixture of 20 ml of water and 20 ml of toluene was charged to the reaction mass. Organic and aqueous layers were separated and the aqueous layer was extracted with 20 ml of toluene. Both of the organic layers were combined followed by washing with 2×20 ml of water. Organic and aqueous layers were separated and the organic layer containing 2-(R)-(1-(R)-(3,5-bis(trifluoromethyl)phenyl)ethoxy)-3-(S)-4-fluorophenyl-4-(2-(N-methylcarboxy-actamidrazono)morpholine of Formula II and 300 ml of toluene were charged into a clean and dry autoclave vessel followed by heating to about 120° C. under closed conditions for about 3 hours. After completion of the reaction, the reaction solution was cooled to about 30° C. and the solvent was distilled completely at about 95° C. under vacuum to afford the title compound in the form of thick syrup. 10 ml of acetonitrile was charged to the residue and the resultant solution was cooled to about 0° C. and was stirred for about 2 hours. Separated solid was filtered and the solid was washed with 2 ml of acetonitrile followed by drying the solid obtained at about 55° C. to afford 1.1 g of the title compound in pure form.

Specific optical rotation (SOR) $[\alpha]_D^{25}$=+61.81° (C=1.0% MeOH);

Purity by RS HPLC: 95.73%;

Purity by chiral HPLC: 99.32%.

Example 9

Alternative Process for the Preparation of Aprepitant (Formula I)

1 g of 2-(R)-(1-(R)-(3,5-bistrifluoromethyl) phenyl) ethoxy-3-(S)-(4-fluorophenyl) morpholine of Formula IIb, 400 ml of acetonitrile, 5 ml of N,N-diisopropylethylamine and 0.45 g of N-methylcarboxy-2-chloroacetamidarazone of Formula III were charged into a clean and dry autoclave vessel followed by heating to about 120° C. The reaction mixture was stirred at about 120° C. for about 3 hours. After the completion of the reaction, the reaction solution was cooled to about 30° C. followed by distillation of the solvent completely at about 70° C. under vacuum to afford 0.8 g of the title compound.

Example 10

Alternative Process for the Preparation of Aprepitant (Formula I)

10 g of the compound of Formula IIb obtained from Example 6 and 30 ml of N,N-dimethylformamide (DMF) were charged into a clean and dry 4 neck round bottom flask followed by stirring for about 10 minutes. The reaction solution was cooled to about 0° C. and a mixture of 3.5 g of potassium carbonate and 1 ml of water was charged. To the resultant reaction mixture a solution of 3.7 g of 3-chloromethyl-1,2,4-triazolin-5-one of Formula (IIe) dissolved in 10 ml of N,N-dimethylformamide (DMF) was charged followed by stirring at about 0° C. for about 4 hours. After the completion of the reaction, 100 ml of water was charged followed by stirring for about 30 minutes. The separated solid was filtered and the solid was washed with 20 ml of water. The solid obtained was dried at about 60° C. for about 3 hours to afford 8 g of aprepitant of Formula I.

Specific optical rotation (SOR): $[\alpha]_D^{25}=+61.18°$ (C=0.68% MeOH);

Purity by RS HPLC: 94.36%;

Purity by chiral HPLC: (+)-cis isomer: 97.12%; (−)-cis isomer: 2.87%.

Example 11

Purification of Aprepitant (Formula I)

4 g of aprepitant of Formula I with RS purity by HPLC 84.53% and 40 ml of acetonitrile were charged into a clean and dry 4 neck round bottom flask followed by heating to about 60° C. The resultant solution was stirred at about 60° C. for about 1 hour followed by cooling to about 30° C. for about 2 hours. The resultant suspension was filtered and the solid obtained was washed with 20 ml of acetonitrile. The solid obtained was dried at about 60° C. under vacuum for about 3 hours to afford 3 g of pure aprepitant.

RS purity by HPLC: 98.48%.

Example 12

Preparation of 2-(N-Benzyl-N-(2-Hydroxyethyl) Amino)-2-(4-Fluorophenyl)Acetamide (Formula X)

5 g of [Benzyl-(2-hydroxyethyl)-amino]-(4-fluorophenyl)-acetonitrile of Formula XI and 15 ml of dimethylsulfoxide (DMSO) were charged in a clean and dry 4 neck round bottom flask followed by stirring for about 20 minutes. 3.8 g. of potassium carbonate was charged to the above reaction solution followed by addition of 7 ml of 50% hydrogen peroxide over about 30 minutes. The resultant reaction solution was stirred for about 2 hours, after completion of the reaction, reaction was quenched by adding 50 ml of water over about 30 minutes. The reaction suspension was stirred for about 1 hour. Separated solid was filtered and the solid was washed with 10 ml of water. Wet cake obtained and 50 ml of petroleum ether were charged in a clean and dry 4neck round bottom flask followed by stirring for about 15 minutes. The solid was filtered and the solid was dried at about 30° C. for about 5 hours to yield 3.8 g of the title compound.

Example 13

Preparation of N-Benzyl-3-(4-Fluorophenyl)-1,4-Oxazin-2-One (Formula IX)

20 g of 2-(N-benzyl-N-(2-hydroxyethyl) amino)-2-(4-fluorophenyl) acetamide of Formula X, 200 ml of acetone and 10 g of L-(+)-tartaric acid were charged in a clean and dry 4 neck round bottom flask. The resultant reaction suspension was heated to reflux followed by stirring for about 3 hours. The reaction solution was cooled to about 30° C. followed by filtration of the solid and the solid was washed with 40 ml of acetone. Filtrate was distilled completely at about 50° C. under vacuum, to the residue 200 ml of dichloromethane, 30 ml of water and 3 g of sodium carbonate were charged followed by stirring for about 15 minutes. Organic and aqueous layers were separated and the organic layer was washed with 30 ml of water. Organic and water layer were separated and 70% of the solvent on the total volume was distilled at about 45° C. under vacuum followed by addition of 10 ml of dilute hydrochloric acid. The resultant acidified organic layer was distilled completely at about 45° C. under vacuum. 100 ml of acetone was charged to the residue and was stirred for about 30 minutes. Separated solid was filtered and the solid was washed with 40 ml of acetone. The resultant wet solid was charged in a clean and dry 4 neck round bottom flask followed by charging of 200 ml of dichloromethane, 30 ml of water and 3 g of sodium carbonate. Resultant reaction suspension was stirred for about 15 minutes, followed by separation of organic and aqueous layers. Organic layer was washed with 30 ml of water. Organic and water layers were separated and the organic layer was distilled completely at about 40° C. under vacuum to yield 16 g of the title compound.

Example 14

Purification of Aprepitant (Formula I) Using Toluene 5 g of aprepitant crude with 89.13% purity by high performance liquid chromatography (HPLC) and 25 ml of toluene were charged in a clean and dry 4 neck round bottom flask followed by heating to about 65° C. for about 2 hours. The resultant solution was cooled to about 30° C. followed by stirring for about 3 hours. Solid separated was filtered and the solid was washed with 25 ml of toluene followed by drying the solid obtained at about 45° C. for about 5 hours to afford 1.6 g of the title compound.

Purity by HPLC: 98.09%.

Example 15

Process for the Purification of Aprepitant (Formula I) Using Acetonitrile 5 g of aprepitant crude with 89.13% purity by high performance liquid chromatography (HPLC) and 25 ml of acetonitrile were charged in a clean and dry 4neck round bottom flask followed by heating to about 65° C. for about 2 hours. The resultant solution was cooled to about 30° C. followed by stirring for about 3 hours. Solid separated was filtered and the solid was washed with 25 ml of acetonitrile followed by drying the solid obtained at about 45° C. for about 5 hours to afford 1.8 g of the title compound.

Purity by HPLC: 97.36%.

Example 16

Process for the Purification of Aprepitant (Formula I) Using Isopropyl Alcohol 5 g of aprepitant crude of 89.13% purity by high performance liquid chromatography (HPLC) and 25 ml of isopropyl alcohol were charged in a clean and dry 4neck round bottom flask followed by heating to about 70° C. for about 2 hours. The resultant solution was cooled to about 30° C. followed by stirring for about 5 hours. Solid separated was filtered and the solid obtained was washed with 25 ml of isopropyl alcohol followed by drying the solid obtained at about 45° C. for about 5 hours to afford 1.4 g of the title compound.

Purity by HPLC: 95.06%.

Example 17

Purification of Aprepitant (Formula I) Using Methyl Tertiary-Butyl Ether 5 g of aprepitant crude of 89.13% purity by high performance liquid chromatography (HPLC) and 25 ml of methyl tertiary-butyl ether were charged in a clean and dry 4neck round bottom flask followed by heating to about 60° C. for about 1-2 hours. The resultant solution was cooled to about 30° C. followed by stirring for about 3 hours. Solid separated was filtered and the solid was washed with 25 ml of methyl tertiary-butyl ether followed by drying the solid obtained at about 45° C. for about 5 hours to afford 0.5 g of the title compound.

Purity by HPLC: 98.34%.

Example 18

Process for the Purification of Aprepitant (Formula I) Using Dichloromethane 5 g of aprepitant crude of 89.13% purity by high performance liquid chromatography (HPLC) and 25 ml of dichloromethane were charged in a clean and dry round bottom flask followed by heating to about 45° C. for about 2 hours. The resultant solution was cooled to about 30° C. followed by stirring for about 3-4 hours. Solid separated was filtered and the solid obtained was washed with 25 ml of dichloromethane followed by drying the solid obtained at about 45° C. for about 5 hours to afford 1.8 g of the title compound.

Purity by HPLC: 98.15%.

Example 19

Process for the Purification of Aprepitant (Formula I) Using Chloroform 5 g of aprepitant crude of 89.13% purity by high performance liquid chromatography (HPLC) and 25 ml of chloroform were charged in a clean and dry round bottom flask followed by heating to about 60° C. for about 2 hours. The resultant solution was cooled to about 30° C. followed by stirring for about 3 hours. Solid separated was filtered and the solid obtained was washed with 25 ml of chloroform followed by drying the solid obtained at about 45° C. for about 4-5 hours to afford 1.8 g of the title compound.

Purity by HPLC: 98.01%.

Example 20

Isolation of Aprepitant (Formula I) in Acetonitrile and Water in the Ratio of 1:1

7 g of aprepitant crude 89.13% and 70 ml of acetonitrile+water (1:1 ratio) were charged in a clean and dry round bottom flask followed by heating to about 65° C. for about 2 hours. The resultant solution was cooled to about 30° C. followed by stirring for about 2 hours. Solid separated was filtered and the solid was subjected to suction over about 15 minutes to afford 1.2 g of the title compound.

Purity by HPLC: 95.3%.

0.8 g of above obtained solid and 20 ml of a mixture of acetonitrile and water (1:1 ratio) were charged in a clean and dry round bottom flask followed by heating to about 45° C. and 0.2 g of charcoal carbon was charged under stirring. The resultant suspension was further heated to about 65° C. and stirred for about 30 minutes. Suspension was filtered through celite and the celite was washed with 10 ml of acetonitrile and water (1:1 ratio) followed by charging the filtrate into a clean and dry round bottom flask and then stirring overnight. The separated solid was filtered and dried aerially for about 2-3 hours to afford 0.5 g of the title compound.

Purity by HPLC: 95.93%.

Example 21

Preparation of Spiro Derivative of Aprepitant (Formula IIc)

3 g of (6R-6-{(1R)-1-[3,5-bis(trifluoromethyl)phenyl]ethoxy}-5-(4-fluorophenyl)-3,6-dihydro-2H-[1,4]oxazine) of Formula IIa and 150 ml of xylene were charged into a clean and dry round bottom flask followed by stirring for about 10 minutes. The resultant reaction suspension was heated to about 95° C. for about 4-5 hours, after completion of the reaction, the solution was cooled to about 80° C. Solvent from the solution was distilled completely at about 95° C. to afford a crude form of the title compound. The above obtained crude form and 10 ml of petroleum ether were charged into a clean and dry round bottom flask followed by stirring for about 2 hours. The resultant suspension was cooled to about 5° C. for about 1-2 hours followed by filtration of the solid and the solid was washed with 5 ml of petroleum ether. Solid obtained was dried at about 55° C. for about 6 hours to afford 2.2 g of title compound with purity by HPLC: 89.86%, Mass (m/z): 436 by LCMS.

$^1$HNMR (200 MHz, CDCl$_3$): δ 0.89 (d, 6H), 1.35 (t, 3H, J=7.4 Hz), 1.4 (t, 3H, J=7.4 Hz), 1.4-1.8 (m, 6H), 1.6 (q, 2H, J=7.4 Hz), 1.7 (m, 1H), 2.63 (m, 1H), 2.91 (m, 2H), 3.5 (s, 2H), 4.0 (m, 2H), 5.35 (m, 1H), 6.81 (d, 1H, J=6.8 Hz), 6.83 (s, 1H), 7.0-7.3 (m, 4H), 7.72 (d, 1H, J=8.2 Hz); $^{13}$C NMR (200 MHz, CDCl$_3$): δ 14.21, 14.59, 22.4, 22.7, 24.0, 24.9, 26.6, 44.1, 46.6, 49.5, 54.8, 60.6, 64.5, 113.8, 120.7, 122.6, 124.9, 127.5, 127.8, 131.9, 138.6, 141.0, 152.4, 158.7 (2C), 166.1, 168.7;

MS: m/z=481 (M$^+$+1).

Example 22

Process for the Purification of 6R-6-{(1R)-1-[3,5-(Trifluoromethyl)Phenyl]Ethoxy}-5-(4-Fluorophenyl)-3,6-Dihydro-2H-[1,4]Oxazine (Formula IIa)

13 g of 6R-6-{(1R)-1-[3,5-(trifluoromethyl) phenyl]ethoxy}-5-(4-fluorophenyl)-3,6-dihydro-2H-[1,4]oxazine of Formula IIa and 50 ml of isopropyl alcohol were charged into a clean and dry round bottom flask followed by heating to about 50° C. for about 30 minutes. The resultant solution was cooled to about 0° C. for about 2 hours followed by filtration of the separated solid and the solid washed with 15 ml of isopropyl alcohol. Solid obtained was dried at about 45° C. for about 3 hours to afford 7.5 grams crude compound of Formula IIa.

Charged above obtained crude compound of Formula IIa and 50 ml of toluene into a clean and dry round bottom flask followed by heating to about 100° C. over about 15 hours.

Solvent from the mass was distilled completely at about 60-65° C. to afford 7.5 grams of crude compound of Formula IIa.

3 grams from the above obtained crude and 23 ml of methanol were taken into a clean and dry round bottom flask followed by stirring for about 15 minutes. The resultant solution was cooled to about 0° C. followed by addition of 0.19 g of sodium borohydride over about 10 minutes. The reaction was stirred for about 1-2 hours followed by allowing the reaction to reach 30° C. After the completion of the reaction, the solvent was distilled completely at about 45° C. To the residue, 30 ml of water and 11 ml of toluene were charged followed by stirring for about 30-minutes. Organic and aqueous layers were separated and the aqueous layer was extracted with 2×11 ml of toluene followed by combining of organic layers. Total organic layer was washed with 2×9 ml of water followed by separation of organic and aqueous layers.

Organic layer was distilled completely at about 55° C. to afford 2.3 g of crude form of the title compound. The obtained crude and 12.5 ml of methanol were charged into a clean and dry round bottom flask followed by stirring for about 30 minutes. 0.63 g of oxalic acid was charged followed by stirring for about 60 minutes and the resultant reaction solution was cooled to about 10° C. for about 2 hours. The separated solid was filtered and the solid was washed with 12.5 ml of methanol. The solid obtained was dried at about 55° C. over about 7 hours to afford 1.9 g of title compound, as the oxalate salt that can be used in a reaction to form the compound having Formula IIb.

Purity by HPLC: 99.19% and the spiro derivative of Formula IIc at 0.95 relative retention time (RRT) was not detectable.

Example 23

Preparation of the Compound of Formula IVa 20 g of the compound of Formula V and 120 ml of N,N-dimethylformamide were charged into a clean and dry round bottom flask and was stirred for about 5-10 minutes. To the resulting solution 1.8 g of potassium carbonate was added and the reaction mass was cooled to about 0° C. 8.0 g of N-chlorosuccinamide was added in small portions over a period of 20 minutes and the resultant reaction mass was stirred for about 30 minutes followed by addition of 9.0 g of 1,8-diazabicyclo[5.4.0]-undec-7-ene (DBU) over 10 minutes. The reaction mass was allowed to reach 3° C. and was stirred for about 3 hours. After completion of the reaction, 200 ml of water and 200 ml of toluene were charged under stirring and organic and aqueous layers were separated. The aqueous layer was extracted with 2×100 ml of toluene and combined organic layers were washed with 3×100 ml of water. The organic layer was dried over anhydrous sodium sulphate and distilled completely under vacuum to afford 16.8 g of the title compound.

Example 24

Preparation of the Compound of Formula IIIa 16 g of the compound of Formula IVa obtained from Example 23, 16 g of 5% palladium on carbon, and 160 ml of methanol were charged into a clean and dry hydrogenation vessel. Dry hydrogen gas of pressure 3.0 kg/cm$^2$ was passed into the reaction suspension for a period of 3 hours at about 30° C. After the completion of the reaction, reaction suspension was filtered through celite and was washed with 80 ml of methanol. The resultant filtrate was distilled completely under vacuum to afford a crude syrup (Formula IIIa). 100 ml of acetonitrile was charged to the residue, left overnight and the separated solid was filtered to obtain 5 g of the title compound.

Specific optical rotation: $[\alpha]_D=0.00°$ (C=1% MeOH);
Purity by RS HPLC: $A_8B_7$ at retention time (RT) 17.1 minutes: 87.39%, $A_7B_8$ at retention time (RT) 19.2 minutes: 8.23%.

Example 25

Preparation of Racemic Aprepitant (Formula IB)

3.0 g of the compound of Formula IIIa obtained from Example 24 and 9.0 ml of N,N-dimethylformamide (DMF) were charged into a clean and dry 4neck round bottom flask followed by stirring for about 10 minutes. Reaction solution was cooled to about 0° C. and a mixture of 1.03 g of potassium carbonate and 0.3 ml of water was charged. To the resultant reaction mass a solution of 1.1 g of 3-chloromethyl-1,2,4-triazolin-5-one of Formula IIe dissolved in 3.0 ml of N,N-dimethylformamide (DMF) was charged followed by stirring at about 0° C. for about 3 hours. After the completion of the reaction 30 ml of water and 30 ml of ethylacetate were charged followed by stirring for about 5 minutes. Organic and aqueous layers were separated and the aqueous layer was extracted with 2×30 ml of ethyl acetate. Combined organic layer was washed with 2×30 ml of water and the resultant organic layer was distilled completely at about 60° C. under vacuum to afford the residue. To the residue 30 ml of acetonitrile was charged and redistilled completely at about 65° C. under vacuum to afford the residue. To the resultant residue 30 ml of acetonitrile was charged and the resultant suspension was stirred at about 30° C. for about 15 minutes. Solid separated was filtered and the solid was washed with 9 ml of acetonitrile followed by drying the solid at about 55° C. for about 6 hours to afford 1.7 g of the title compound.

Specific optical rotation: $[\alpha]_D=0.00°$ (C=0.68% MeOH);
Purity by RS HPLC: 96.0%;
Purity by chiral HPLC: (−)-cis isomer at retention time (RT) 13.13 minutes: 49.95%, (+)-cis isomer at retention time (RT) 15.97 minutes: 50.04%.

Example 26

Preparation of the Compound of Formula IVc 20 g of the compound of Formula IV and 120 ml of N,N-dimethylformamide (DMF) were charged into a clean and dry 4neck round bottom flask followed by stirring for about 5 minutes. To the resultant reaction solution 2.48 g of potassium carbonate was charged and the reaction mass was cooled to about 0° C. 8.0 g of N-chlorosuccinamide (NCS) was added in small portions over about 20 minutes and the resultant reaction mass was stirred for about 30 minutes followed by addition of 9.0 g of 1,8-diazabicyclo-[5.4.0]-undec-7-ene (DBU) over about 5 minutes. Reaction mass was allowed to reach 30° C. followed by stirring for about 3 hours. After completion of the reaction, 200 ml of water and 200 ml of toluene were charged under stirring followed by stirring for about 5 minutes. Organic and aqueous layers were separated followed by extraction of aqueous layer with 2×100 ml of toluene. Both the organic layers were combined and the total organic layer was washed with 3×100 ml of water. Final organic layer was dried over 50 g of anhydrous sodium sulphate and distilled completely at about 100° C. under vacuum to afford 16.0 g of the title compound.

Example 27

Preparation of the Compound of Formula IIIa 15 g of the compound Formula IVc, 15 g of 5% palladium on carbon, and 150 ml of methanol, were charged into a clean and dry hydrogenation vessel. Dry hydrogen gas of pressure 3.0 kg/cm$^2$ was passed into the reaction suspension for a period of 2-3 hours at about 25-35° C. After the completion of the reaction, reaction suspension was filtered through celite and was washed with 40 ml of methanol. The resultant filtrate was distilled completely under vacuum to afford 13 g of the title compound (Formula IIIa).

Example 28

Preparation of Racemic Aprepitant (Formula IB)

5.0 g of the compound of Formula IIIa obtained from Example 27 and 15 ml of N,N-dimethylformamide (DMF) were charged into a clean and dry 4neck round bottom flask and stirred for about 5 minutes. Reaction solution was cooled to about 0° C. and a mixture of 1.8 g of potassium carbonate and 0.5 ml demineralised water was charged. To the resultant reaction mass a solution of 1.8 g of 3-chloromethyl-1,2,4-triazolin-5-one of Formula IIe dissolved in 5 ml of N,N-dimethylformamide (DMF) was charged followed by stirring at about 0° C. for about 3 hours. After the completion of the reaction, 50 ml of water and 50 ml of ethyl acetate were charged. Organic and aqueous layers were separated and the aqueous layer was extracted with 2×50 ml of ethyl acetate. Combined organic layer was washed with 2×50 ml of water and the resultant organic layer was distilled completely at about 65° C. under vacuum to afford the residue. To the resultant residue 50 ml of acetonitrile was charged and the resultant residual suspension was stirred at 30° C. for about 15 minutes. Solid separated was filtered and the solid was washed with 10 ml of acetonitrile. The solid obtained was dried at about 60° C. for about 8 hours to afford 2.8 g of the title compound.

Example 29

Alternative Process for Preparation of (±)-Trans-N-Benzyl-3-(4-Fluorophenyl)-1,4-Oxazin-2-Ol (Formula VIII)

2.5 g of the morpholinone compound of Formula IX and 25 ml of toluene were charged into a clean and dry 4neck round bottom flask followed by stirring for about 5 minutes. 4 ml of sodium dihydro-bis-(2-methoxyethoxy) aluminate ("Vit-ride") (65% in toluene) was added over about 5 minutes followed by stirring at about 30° C. for about 2 hours. After the completion of the reaction, reaction mass was quenched by the addition of 50 ml aqueous hydrochloric acid solution over a period of about 30 minutes followed by separation of organic and aqueous layers. Aqueous layer was extracted with 2×25 ml of toluene followed by separation of aqueous and organic layers. pH of the aqueous layer was adjusted to about 8.5 by the addition of 5 ml of caustic lye followed by extraction with 3×25 ml of toluene. Organic and aqueous layers were separated and the combined organic layer was washed with 3×25 ml of water. Organic layer was dried over sodium sulphate and distilled completely under vacuum to afford the 2 g of the title compound.

Example 30

Alternative Process for Preparation of (±)-Trans-N-Benzyl-3-(4-Fluorophenyl)-1,4-Oxazin-2-Ol (Formula VIII)

5 g of (±)-N-benzyl-3-(4-fluorophenyl)-1,4-oxazin-2-one of Formula IX and 100 ml of methanol were charged into a clean and dry 4neck round bottom flask followed by stirring for about 5 minutes. Resultant reaction solution was cooled to about 0° C. followed by addition of 0.65 g sodium borohydride in small portions over about 15 minutes. The reaction solution was allowed to attain a temperature of about 30° C. followed by stirring for about 2 hours. After completion of the reaction, the reaction mixture was quenched with 200 ml of water. Resultant reaction solution was extracted with 3×100 ml of toluene. Combined organic layers were washed with 3×100 ml of water and the organic phase was dried over 20 g of anhydrous sodium sulphate and the organic layer was distilled completely at about 60° C. under vacuum to afford 4 g of the title compound.

Example 31

Alternative Process for Preparation of (±)-Trans-4-Benzyl-2-[2-(3,5-Bis-Trifluoromethylphenyl)-Ethoxy]-3-(4-Fluorophenyl)Morpholine (Formula VI)

3.76 g of sodium hydride and 300 ml of dimethylsulfoxide (DMSO) were charged into a clean and dry 4neck round bottom flask under nitrogen atmosphere, followed by heating to about 70° C. and was stirred for about 2 hours. Resultant reaction solution was cooled to about 30° C. and a solution of 30 g of (±)-N-benzyl-3-(4-fluorophenyl)-1,4-oxazin-2-ol of Formula VIII dissolved in 60 ml of dimethyl sulfoxide, a solution of 50 g of 1-(1-bromoethyl) 3,5-bis-trifluoromethyl-benzene of Formula VII dissolved in 60 ml of dimethylsulfoxide were charged followed by stirring for about 3 hours. After completion of the reaction, the reaction mass was quenched with 450 ml of precooled water and 300 ml of toluene. Organic and aqueous phases were separated and the aqueous phase was extracted with 2×300 ml of toluene. Combined organic layer was washed with 3×300 ml of water followed by drying the organic layer over 100 g of anhydrous sodium sulphate and the organic layer was distilled completely at about 60° C. under vacuum to afford 40 g of the title compound.

Example 32

Preparation of 2-(R)-(1-(R)-3,5-Bis(Trifluoromethyl)Phenyl)Ethoxy-3-(S)-(4-Fluorophenyl)Morpholine (Formula IIb)

5 g of 6-[1(S)-3,5-bis(trifluoromethylphenyl)ethoxy]-5-(4-fluorophenyl)-3,6-dihydro-2H-[1,4]oxazine of Formula IIa and 35 ml of methanol were charged into a clean and dry round bottom flask followed by stirring for about 5-10 minutes. The resultant solution was cooled to about 0-5° C. followed by charging of 0.45 g of sodium borohydride. The solution was allowed to attain a temperature of about 25-35° C. under stirring over about 25-45 minutes. After completion of the reaction, solvent from the reaction mixture was distilled completely at about 60-65° C. followed by charging 100 ml of a 1:1 by volume mixture of water and dichloromethane. Organic and aqueous layers were separated and the aqueous layer was extracted with 25 ml of dichloromethane. Organic and aqueous layers were separated and both the organic layers were combined followed by washing with 2×50 ml of water. Organic and aqueous layers were separated and the solvent was distilled completely from the organic layer at about 35-40° C. to afford 5 g of the title compound in the form a syrup.

$[\alpha]_D=(+75.37°)$ (0.6% MeOH); RS HPLC Purity: 96.32%

Example 33

Determination of Impurity Formula IIc in the Compound of Formula IIa

TABLE 1

| HPLC conditions for determining impurity of Fomula IIc in compound of Formula IIa. | |
|---|---|
| Column: | Zorbax SB C-18 |
| | 250 × 4.6 × 5.0 µm or equivalent |
| Flow rate: | 1.0 ml/minute |
| Column temperature: | Ambient |
| Detector wavelength: | 210 nm |
| Injection volume: | 20 µl. |
| Mobile phase | Mixture of buffer and acetonitrile in the ratio of 40:60 |
| Run time: | 60 minutes |
| Elution: | Isocratic |

Buffer: Dissolve 1.36 g of potassium dihydrogen phosphate in 1000 ml of water and adjust the pH to 7.0 with dilute KOH solution.

The invention claimed is:

1. A process comprising reducing a compound having the formula:

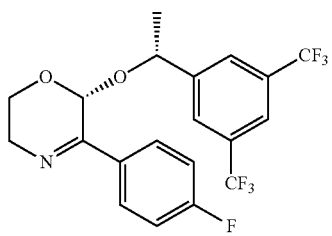

or a salt thereof, with a chemical reducing agent to form a compound having the formula:

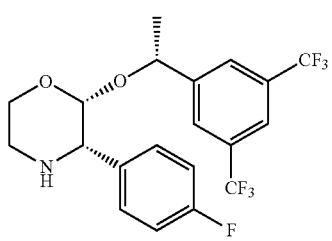

wherein the chemical reducing agent is sodium borohydride, potassium borohydride, sodium dihydro-bis-(2-methoxyethoxy)aluminate, sodium cyanoborohydride, or sodium triacetoxyborohydride.

2. A process comprising reducing a compound having the formula

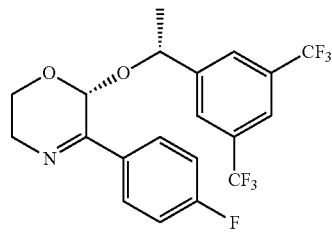

or a salt thereof, with a chemical reducing agent to form a compound having the formula:

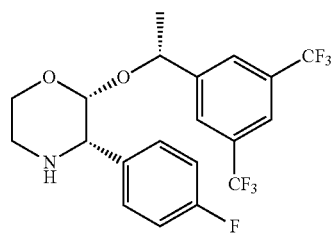

wherein the chemical reducing agent is sodium borohydride, potassium borohydride, sodium dihydro-bis-(2methoxyethoxy)aluminate, sodium cyanoborohydride, or sodium triacetoxyborohydride, further comprising reacting the compound having the formula:

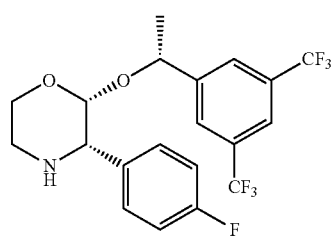

with a compound having the formula:

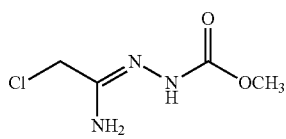

and heating a reaction product to form aprepitant.

3. A process comprising reducing a compound having the formula

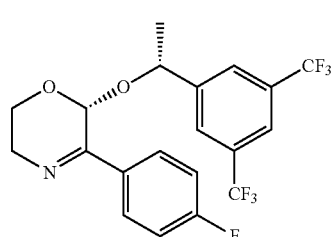

or a salt thereof, with a chemical reducing agent to form a compound having the formula:

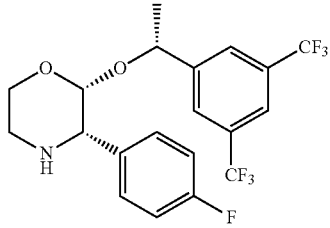

wherein the chemical reducing agent is sodium borohydride, potassium borohydride, sodium dihydro-bis-(2methoxyethoxy)aluminate, sodium cyanoborohydride, or sodium triacetoxyborohydride, further comprising reacting the compound having the formula:

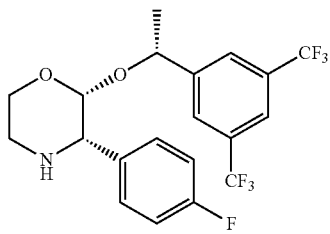

with a compound having the formula:

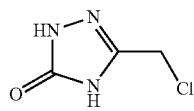

to form a mixture of optical isomers and resolving a mixture to recover aprepitant.

4. The process of claim 1, wherein the chemical reducing agent is sodium borohydride.

5. The process of claim 1, wherein the compound having the formula:

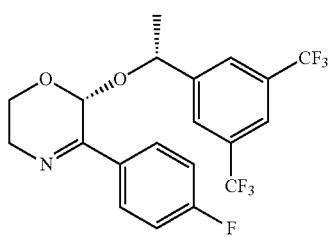

is in the form of a salt.

6. The process of claim 5, wherein the compound having the formula:

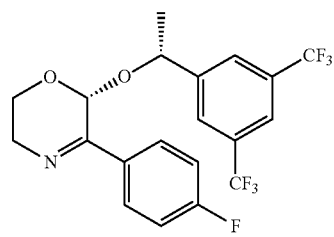

is in the form of an oxalate salt.

7. The process of claim 1, further comprising dehydrogenating a compound having the formula:

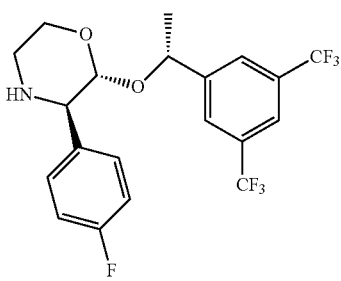

to form the compound having the formula:

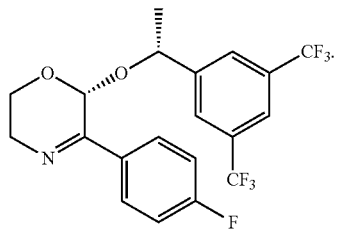

8. The process of claim 2, further comprising dehydrogenating a compound having the formula:

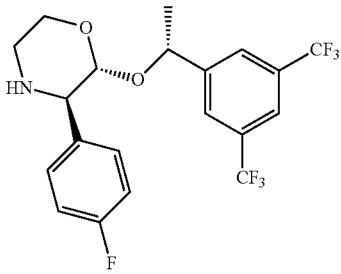

to form the compound having the formula:

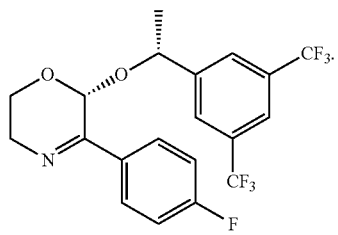

9. The process of claim 8 further comprising debenzylating the isomeric compounds having the formula:

10. The process of claim 9 further comprising reacting a compound having the formula:

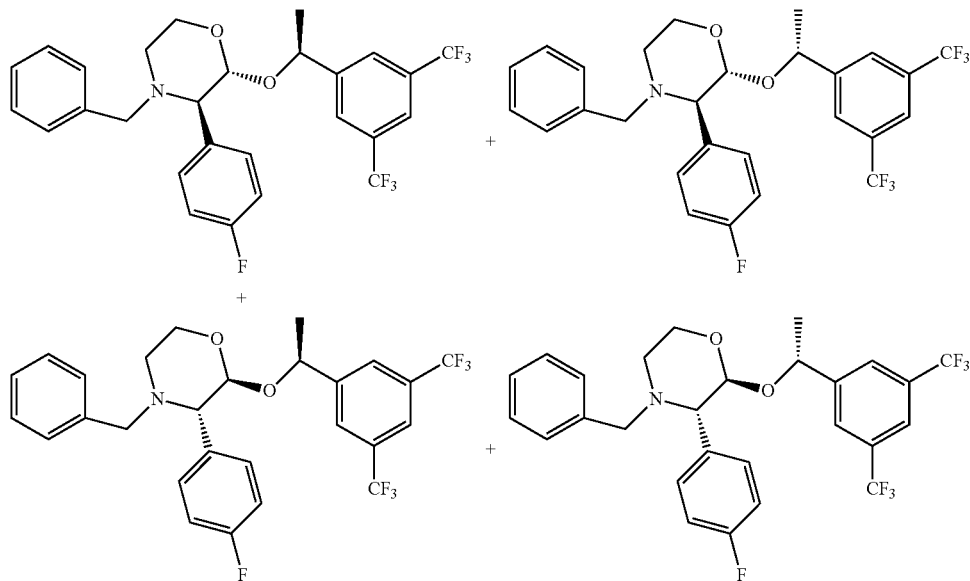

or a salt thereof; performing a diastereomeric crystallization to form the isomeric compounds having the formula:

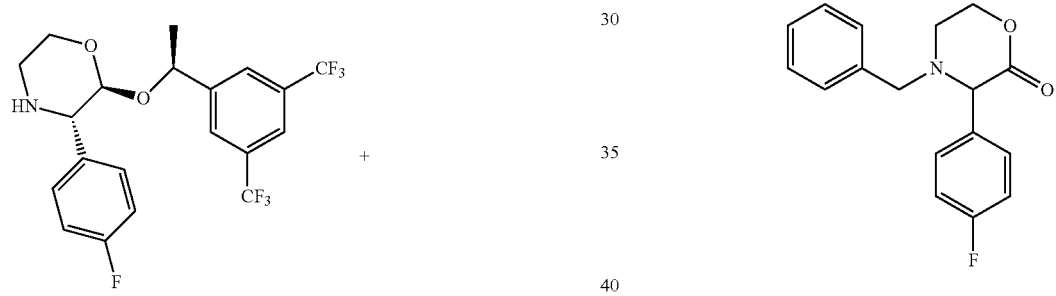

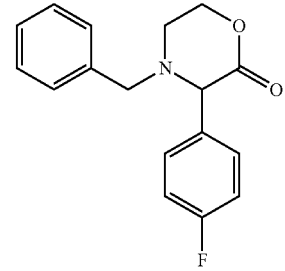

with a selective reducing agent to form the isomeric compounds having the formula:

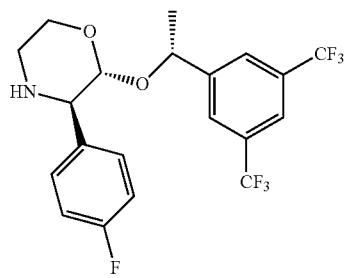

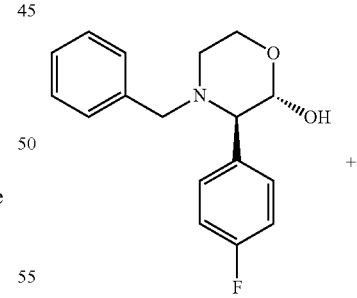

and resolving isomers to obtain the compound having the formula:

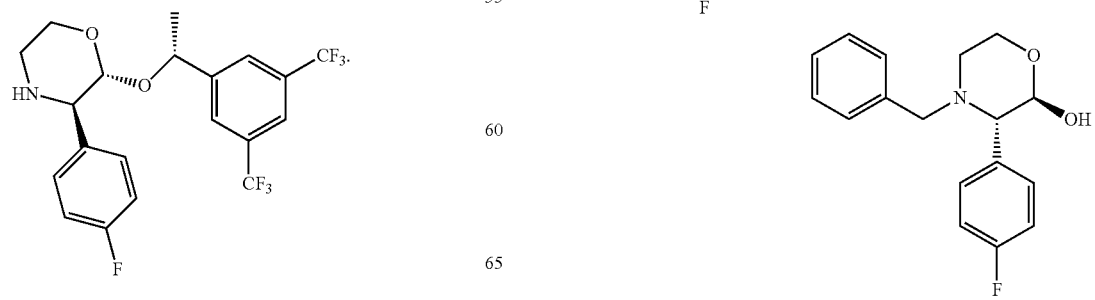

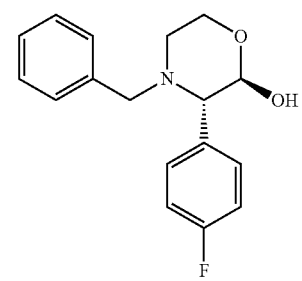

and further reacting with a compound having the formula:

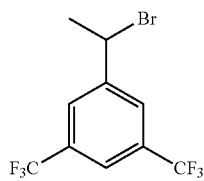

to form the isomeric compounds having the formula:

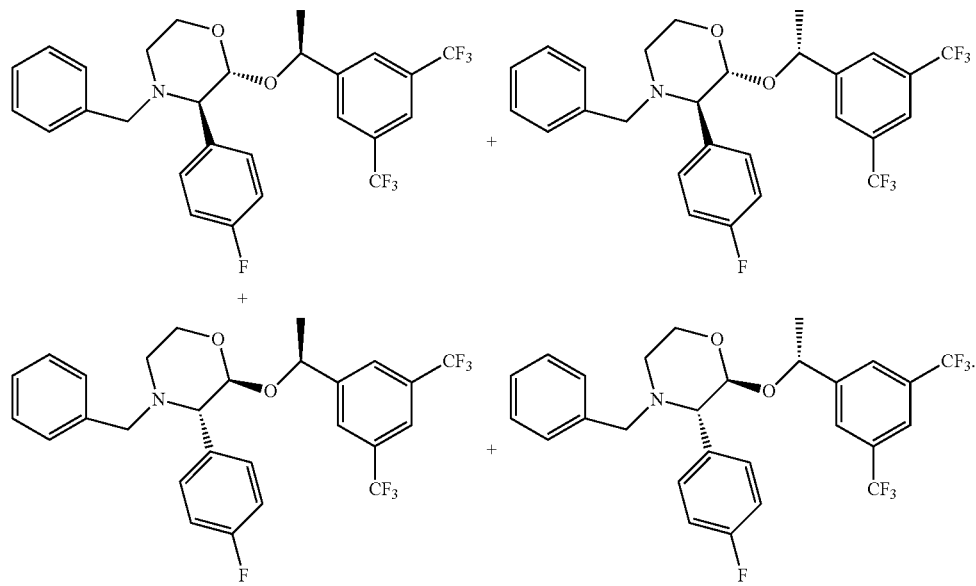

11. The process of claim 10, wherein a selective reducing agent is lithium tri-sec-butylborohydride.

12. The process of claim 9, wherein debenzylating is performed after converting the isomeric compounds to a salt thereof.

13. The process of claim 2, wherein a compound having the formula:

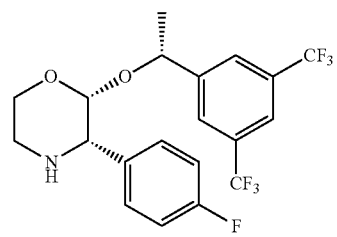

is purified, prior to reacting with a compound having the formula:

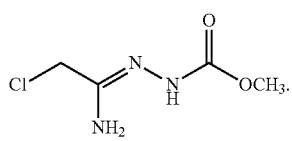

14. The process of claim 13, wherein purifying the compound having the formula:

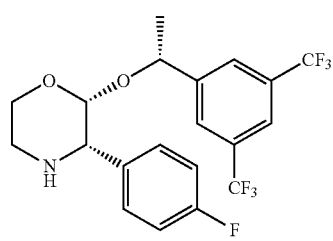

comprises crystallizing from an alcohol, dissolving in a hydrocarbon and removing solvent to form a residue, dissolving a residue in an alcohol and treating with sodium borohydride, removing an alcohol, extracting with a hydrocarbon, and forming an oxalate salt.

* * * * *